(12) United States Patent
Wu et al.

(10) Patent No.: US 9,459,229 B2
(45) Date of Patent: *Oct. 4, 2016

(54) ELECTROCHEMICAL TEST SENSOR

(71) Applicant: Ascensia Diabetes Care Holdings AG, Basel (CH)

(72) Inventors: Huan-Ping Wu, Granger, IN (US); Christine D. Nelson, Edwardsburg, MI (US); Hope Spradlin, Granger, IN (US); Eric Maurer, New Bremen, OH (US)

(73) Assignee: Ascenia Diabetes Care Holdings AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/964,721

(22) Filed: Dec. 10, 2015

(65) Prior Publication Data

US 2016/0084792 A1 Mar. 24, 2016

Related U.S. Application Data

(60) Continuation of application No. 14/252,226, filed on Apr. 14, 2014, now Pat. No. 9,239,312, which is a division of application No. 14/079,922, filed on Nov. 14, 2013, now Pat. No. 8,728,299, which is a division (Continued)

(51) Int. Cl.
*G01N 27/327* (2006.01)
*C12Q 1/00* (2006.01)

(52) U.S. Cl.
CPC ........... *G01N 27/3272* (2013.01); *C12Q 1/004* (2013.01); *C12Q 1/006* (2013.01); *G01N 27/327* (2013.01); *G01N 27/3273* (2013.01); *Y10S 435/817* (2013.01)

(58) Field of Classification Search
CPC .... G01N 27/48; G01N 27/26; G01N 27/327; C12Q 1/00; C12Q 1/02; C12Q 1/34; C12Q 1/54

See application file for complete search history.

(56) References Cited

U.S. PATENT DOCUMENTS 3,791,933 A 2/1974 Moyer
3,791,988 A 2/1974 Dieter
(Continued)

FOREIGN PATENT DOCUMENTS

DE 102005003911 * 8/2005
DE 102005003911 A1 8/2005
(Continued)

OTHER PUBLICATIONS

EPO, Search Report and Written Opinion for PCT/US2007/077955, Dec. 18, 2007, Publisher: International Searching Authority.
(Continued)

*Primary Examiner* — Jennifer Dieterle
(74) *Attorney, Agent, or Firm* — Nixon Peabody LLP

(57) ABSTRACT

The present invention relates to electrochemical sensor strips and methods of determining the concentration of an analyte in a sample or improving the performance of a concentration determination. The electrochemical sensor strips may include at most 8 μg/mm² of a mediator. The strips, the strip reagent layer, or the methods may provide for the determination of a concentration value having at least one of a stability bias of less than ±10% after storage at 50° C. for 4 weeks when compared to a comparison strip stored at −20° C. for 4 weeks, a hematocrit bias of less than ±10% for whole blood samples including from 20 to 60% hematocrit, and an intercept to slope ratio of at most 20 mg/dL. A method of increasing the performance of a quantitative analyte determination also is provided.

24 Claims, 11 Drawing Sheets

Related U.S. Application Data of application No. 12/951,382, filed on Nov. 22, 2010, now Pat. No. 8,702,965, which is a division of application No. 11/853,010, filed on Sep. 10, 2007, now Pat. No. 7,862,696.

(60) Provisional application No. 60/846,688, filed on Sep. 22, 2006.

(56) References Cited

U.S. PATENT DOCUMENTS

| | | | |
|---|---|---|---|
| 4,230,470 A | 10/1980 | Matsuda | |
| 4,711,245 A | 12/1987 | Higgins | |
| 4,746,607 A | 5/1988 | Mura | |
| 5,108,564 A | 4/1992 | Szuminsky | |
| 5,120,420 A | 6/1992 | Nankai | |
| 5,128,015 A | 7/1992 | Szuminsky | |
| 5,206,147 A | 4/1993 | Hoenes | |
| 5,262,035 A | 11/1993 | Gregg | |
| 5,264,104 A | 11/1993 | Gregg | |
| 5,288,387 A | 2/1994 | Ito | |
| 5,288,636 A | 2/1994 | Pollmann | |
| 5,320,725 A | 6/1994 | Gregg | |
| 5,356,786 A | 10/1994 | Heller | |
| 5,393,615 A | 2/1995 | Corey | |
| 5,498,542 A | 3/1996 | Corey | |
| 5,520,786 A | 5/1996 | Bioczynski | |
| 5,545,519 A | 8/1996 | Vadagama | |
| 5,582,697 A | 12/1996 | Ikeda | |
| 5,620,579 A | 4/1997 | Genshaw | |
| 5,628,890 A | 5/1997 | Carter | |
| 5,631,371 A | 5/1997 | Bioczynski | |
| 5,631,863 A | 5/1997 | Fechner | |
| 5,653,863 A | 8/1997 | Genshaw | |
| 5,682,884 A | 11/1997 | Hill | |
| 5,695,947 A | 12/1997 | Guo | |
| 5,708,247 A | 1/1998 | McAleer | |
| 5,762,770 A | 6/1998 | Pritchard | |
| 5,798,031 A | 8/1998 | Charlton | |
| 5,820,551 A | 10/1998 | Hill | |
| RE36,268 E | 8/1999 | Szuminsky | |
| 5,951,836 A | 9/1999 | McAleer | |
| 5,958,199 A | 9/1999 | Miyamoto | |
| 5,997,817 A * | 12/1999 | Crismore | C12Q 1/001 204/403.1 |
| 6,153,069 A | 11/2000 | Pottgen | |
| 6,258,229 B1 | 7/2001 | Winarta | |
| 6,284,125 B1 | 9/2001 | Hodges | |
| 6,287,451 B1 | 9/2001 | Winarta | |
| 6,297,697 B2 | 10/2001 | Delano | |
| 6,413,398 B1 | 7/2002 | Gerhardt | |
| 6,413,411 B1 | 7/2002 | Pottgen | |
| 6,475,372 B1 | 11/2002 | Ohara | |
| 6,484,046 B1 | 11/2002 | Say | |
| 6,911,131 B2 | 6/2005 | Miyazaki | |
| 7,138,041 B2 | 11/2006 | Su | |
| 7,163,616 B2 | 1/2007 | Vreeke | |
| 7,288,174 B2 | 10/2007 | Cui | |
| 7,641,785 B2 | 1/2010 | Shinno | |
| 7,862,696 B2 | 1/2011 | Wu | |
| 8,105,478 B2 | 1/2012 | Barlag | |
| 8,147,674 B2 | 4/2012 | Wu | |
| 8,702,965 B2 | 4/2014 | Wu | |
| 8,728,299 B2 | 5/2014 | Wu | |
| 9,239,312 B2 | 1/2016 | Wu | |
| 2001/0006149 A1 | 7/2001 | Taniike | |
| 2005/0016844 A1 | 1/2005 | Burke | |
| 2007/0034512 A1 | 2/2007 | Yamaoka | |
| 2008/0099347 A1* | 5/2008 | Barlag | G01N 27/3277 205/793.5 |
| 2008/0173552 A1 | 7/2008 | Wu | |
| 2008/0179197 A1 | 7/2008 | Wu | |
| 2009/0152128 A1 | 6/2009 | Chu | |

FOREIGN PATENT DOCUMENTS

| | | |
|---|---|---|
| EP | 0330517 | 2/1989 |
| EP | 0354441 | 2/1990 |
| EP | 1074832 | 2/2001 |
| EP | 1691192 | 3/2004 |
| EP | 1707953 | 4/2006 |
| EP | 1742045 | 1/2007 |
| WO | WO 88/03270 | 5/1988 |
| WO | WO 98/35225 | 8/1998 |
| WO | WO 2005/040407 * | 5/2005 |
| WO | WO 2006/042304 | 4/2006 |
| WO | WO 2006/096619 | 9/2006 |
| WO | WO 2009/076433 | 6/2009 |

OTHER PUBLICATIONS

Fultz, et al., "Mediator Compounds for the Electrochemical Study of Biological Redox System: A Compilation", "Analytica Chimica Acta", 1982, pp. 118, vol. 140.

Ho et al., "Electrochemical Sensor for Measurements of Urea and Creatinine in Serum Based on Ac Impedance Measurement of Enzyme-Catal", Anal Chem, 1999, pp. 1940-1946, vol. 71.

Razumiene et al., "Improvement of Screen-Printed Carbon Electrodes by Modifications with Ferreocene Derivative", "Sensors and Actuators B. Elesvier Sequioa", 2003, pp. 378-383, vol. 95, No. 1-3.

A.D. Smith, Ed., "Oxford Dictionary of Biochemistry and Molecular Biology, Revised Edition", 2000, pp. 161 476, 477, 560, Publisher: Oxford University Press.

* cited by examiner

ELECTROCHEMICAL TEST SENSOR

REFERENCE TO RELATED APPLICATIONS

This application is a continuation of U.S. patent application Ser. No. 14/252,226 filed Nov. 14, 2013, which has been allowed; U.S. patent application Ser. No. 14/252,226 is a divisional of U.S. application Ser. No. 14/079,922 filed Nov. 14, 2013 and issued as U.S. Pat. No. 8,728,299; U.S. application Ser. No. 14/079,922 is a divisional of U.S. application Ser. No. 12/951,382 filed Nov. 22, 2010 and issued as U.S. Pat. No. 8,702,965; U.S. application Ser. No. 12/951,382 is a divisional of U.S. application Ser. No. 11/853,010 filed Sep. 10, 2007 and issued as U.S. Pat. No. 7,862,696, which claims the benefit of U.S. Provisional Application No. 60/846,688 entitled "Biosensor System Having Enhanced Stability and Hematocrit Performance" filed Sep. 22, 2006, all of which are incorporated by reference in their entireties.

BACKGROUND

Biosensors provide an analysis of a biological fluid, such as whole blood, urine, or saliva. Typically, a biosensor analyzes a sample of the biological fluid to determine the concentration of one or more analytes, such as glucose, uric acid, lactate, cholesterol, or bilirubin, in the biological fluid. The analysis is useful in the diagnosis and treatment of physiological abnormalities. For example, a diabetic individual may use a biosensor to determine the glucose level in whole blood for adjustments to diet and/or medication.

Biosensors may be implemented using bench-top, portable, and like devices. The portable devices may be handheld. Biosensors may be designed to analyze one or more analytes and may use different volumes of biological fluids. Some biosensors may analyze a single drop of whole blood, such as from 0.25-15 microliters ($\mu L$) in volume. Examples of portable measurement devices include the Ascensia Breeze® and Elite® meters of Bayer Corporation; the Precision® biosensors available from Abbott in Abbott Park, Ill.; Accucheck® biosensors available from Roche in Indianapolis, Ind.; and OneTouch Ultra® biosensors available from Lifescan in Milpitas, Calif. Examples of bench-top measurement devices include the BAS 100B Analyzer available from BAS Instruments in West Lafayette, Ind.; the CH Instruments' Electrochemical Workstation available from CH Instruments in Austin, Tex.; the Cypress Electrochemical Workstation available from Cypress Systems in Lawrence, Kans.; and the EG&G Electrochemical Instrument available from Princeton Research Instruments in Princeton, N.J.

Biosensors usually measure an electrical signal to determine the analyte concentration in a sample of the biological fluid. The analyte typically undergoes an oxidation/reduction or redox reaction when an input signal is applied to the sample. An enzyme or similar species may be added to the sample to enhance the redox reaction. The input signal usually is an electrical signal, such as a current or potential. The redox reaction generates an output signal in response to the input signal. The output signal usually is an electrical signal, such as a current or potential, which may be measured and correlated with the concentration of the analyte in the biological fluid.

Many biosensors have a measurement device and a sensor strip. A sample of the biological fluid is introduced into a sample chamber in the sensor strip. The sensor strip is placed in the measurement device for analysis. The measurement device usually has electrical contacts that connect with electrical conductors in the sensor strip. The electrical conductors typically connect to working, counter, and/or other electrodes that extend into a sample chamber. The measurement device applies the input signal through the electrical contacts to the electrical conductors in the sensor strip. The electrical conductors convey the input signal through the electrodes into a sample deposited in the sample chamber. The redox reaction of the analyte generates an output signal in response to the input signal. The measurement device determines the analyte concentration in response to the output signal.

The sensor strip may include reagents that react with the analyte in the sample of biological fluid. The reagents may include an ionizing agent for facilitating the redox reaction of the analyte, as well as mediators or other substances that assist in transferring electrons between the analyte and the conductor. The ionizing agent may be an oxidoreductase, such as an analyte specific enzyme, which catalyzes the oxidation of glucose in a whole blood sample. The reagents may include a binder that holds the enzyme and mediator together.

One disadvantage of the reagent compositions used in conventional biosensors is the change in measurement performance, either accuracy or precision, that occurs when the sensor strip is stored. The electronics and analysis methods used by the measurement device to determine the analyte concentration of the sample are generally selected in view of the reagent composition on the sensor strip performing as initially manufactured. However, after transportation and storage on store shelves, the reagent composition degrades with time and temperature. This change in the chemistry of the reagent composition may result in a reduction of measurement performance.

To increase the long-term stability of biosensor reagent compositions, conventional biosensors generally rely on a substantial excess of enzyme and mediator in relation to the amount of these reagents required to analyze the sample. Expecting these reagents to degrade over time, conventional reagent compositions include substantially greater amounts of enzyme and/or mediator than required to stoichiometrically react with the analyte. In addition to increasing the cost of the biosensor through the use of sacrificial reagents, the unnecessary reagents may require a larger sample volume, longer analysis time, and decrease the measurement performance of the biosensor due to many factors.

For example, PCT publication WO 88/03270 discloses an overall deposition density of 3 mg/cm$^2$ (30 $\mu$g/mm$^2$) with a screen printing method. The relative amount of $K_3Fe(CN)_6$ was 57.7%, phosphate buffer at 28.8%, and glucose oxidase (GO) at 3.6%. Translating these percentages into deposition densities on the sensor strip results in a $K_3Fe(CN)_6$ density of 17.31 $\mu$g/mm$^2$, a phosphate buffer density of 8.64 $\mu$g/mm$^2$, and a GO density of 1.08 $\mu$g/mm$^2$. In another example, column 17, lines 25-35 of U.S. Pat. No. 4,711,245 discloses the deposition of 15 $\mu$L of a 0.1 M solution of 1,1'-dimethylferrocene in toluene onto a disk electrode having a diameter of 4 mm. With a molecular weight of 214 M.U., the 1,1'-dimethylferrocene mediator was applied at a deposition density of 25.5 $\mu$g/mm$^2$ [(15 $\mu$L*0.1M*214 g/mol)/2$^2$*3.14 mm$^2$=25.5 $\mu$g/mm$^2$]. In a further example, U.S. Pat. No. 5,958,199 discloses the deposition onto the sensor electrode of 4 $\mu$L of a solution including 40 mg of GO, 16 mg of $K_3Fe(CN)_6$, and 20 mg of CMC in 1 mL of water. In this instance, the deposition densities were 6.67 $\mu$g/mm$^2$ for GO, 10.67 $\mu$g/mm$^2$ for $K_3Fe(CN)_6$, and 13.33 $\mu$g/mm$^2$ for CMC with an estimated electrode area (deposition area) of 6 mm$^2$. In a further example, U.S. Pat. No. 5,997,817 describes a reagent formulation including 59 g of $K_3Fe(CN)_6$ dissolved in approximately 900 mL water with other ingredients. Approximately 4.5 μL of this reagent was deposited onto a 21.4 mm$^2$ (3.2×6.7) opening to give a mediator deposition density of 13.96 μg/mm$^2$ (4.5×10$^{-3}$ mL*59 g/900 mL).

In each of these examples, the reagent compositions had mediator deposition densities in the 10-25 μg/mm$^2$ range, while the enzyme deposition density was in the 1-6 μg/mm$^2$ range. This large mediator loading in relation to the enzyme may be attributable to the single application of the composition to both the working and counter electrodes. Depending on sensor design, mediator may function at the counter electrode to support the electrochemical activity at the working electrode. Thus, a single reagent composition deposition covering both electrodes may result in substantially overloading the working electrode with mediator.

The examples show that excesses of enzyme and mediator are used to ensure that enough active ingredients are present for accurate glucose measurement. Using sensor strips manufactured with increased sacrificial amounts of reagents after long-term storage may result in the disadvantage of a drift in measurement performance. This drift may be observed in at least two ways: (1) a background current increase over time (affecting the calibration intercept) and (2) a shift in sensor sensitivity (affecting the calibration slope).

During storage, reduced mediator may be produced from interactions between the oxidized mediator and the enzyme system and polymer. This is a natural process believed to be governed by thermodynamics. The larger the amount of mediator or enzyme, the larger the amount of reduced mediator that is produced. As the concentration of reduced mediator increases over time, the background current will increase toward the end of the shelf-life of the sensor strips.

Multiple methods have been proposed to reduce the effect of drift on sensor performance before use of a stored sensor strip. For example, Genshaw et al. in U.S. Pat. No. 5,653,863 disclosed a method of using a relatively long initial pulse before the analysis to oxidize mediator that was reduced during transport and storage. While effective, this method lengthened the time required to complete the analysis.

Thus, it would be desirable to increase the long-term stability of the reagent composition to improve the measurement performance of the biosensor after transportation and storage. Such a long-term stability increase of the reagent composition may increase the measurement performance of the biosensor and provide a longer shelf-life for the sensor strips. It also would be desirable to reduce the amount of sacrificial enzyme and/or mediator included in the reagent composition and to decrease the time required to complete the analysis.

Another drawback of conventional biosensors used to measure the glucose concentration in whole blood (WB) samples is referred to as the "hematocrit effect." In addition to water and glucose, WB samples contain red blood cells (RBC). Hematocrit is the volume of a WB sample occupied by RBC in relation to the total volume of the WB sample and is often expressed as a percentage. The hematocrit effect occurs when red blood cells block the diffusion of the analyte and/or mediator to one or more electrodes of the biosensor. Since the output signal measured by the biosensor corresponds to the rate of diffusion of the analyte and/or mediator, the RBC may introduce error to the analysis by interfering with this diffusion process. Thus, the greater the hematocrit percent (volume of red blood cells) deviates from the %-hematocrit system calibration for a WB sample, the greater the hematocrit bias (error) in the glucose readings obtained from the biosensor.

WB samples generally have hematocrit percentages ranging from 20 to 60%, with ~40% being the average. If WB samples containing identical glucose levels, but having hematocrits of 20, 40, and 60%, are tested, three different glucose readings will be reported by a system based on one set of calibration constants (slope and intercept of the 40% hematocrit containing WB sample, for instance). Even though the glucose concentrations are the same, the system will report that the 20% hematocrit WB sample contains more glucose than the 40% hematocrit WB sample, and that the 60% hematocrit WB sample contains less glucose than the 40% hematocrit WB sample due to the RBC interfering with diffusion of the analyte and/or mediator to the electrode surface. Thus, conventional biosensors may not be able to distinguish between a lower analyte concentration and a higher analyte concentration where the RBC interfere with diffusion.

Conventional biosensors are generally configured to report glucose concentrations assuming a 40% hematocrit content for the WB sample, regardless of the actual hematocrit content. For these systems, any glucose measurement performed on a blood sample containing less or more than 40% hematocrit will include some hematocrit bias attributable to the hematocrit effect.

Various methods and techniques have been proposed to reduce the bias of the hematocrit effect on glucose measurements. For example, Ohara et al. in U.S. Pat. No. 6,475,372 disclosed a method of using the ratio of currents from a forward and a reverse potential pulse to compensate for the hematocrit effect. McAleer et al. in U.S. Pat. Nos. 5,708,247 and 5,951,836 disclosed a reagent formulation using silica particles to filter the RBC from the electrode surface for reducing the hematocrit effect. Carter et al. in U.S. Pat. No. 5,628,890 disclosed a method of using wide electrode spacing in combination with mesh layers to distribute the blood sample to reduce the hematocrit effect.

These conventional techniques for reducing the bias attributable to the hematocrit effect included (a) co-deposition of a polymer to minimize the hematocrit effect, (b) addition of various kinds of fused silica to enhance the filtration effect for the polymer layer, (c) compensation coefficients based on the ratio of currents from a forward and a reverse potential pulse, and (d) self-compensation by utilizing the existing solution resistance of the whole blood samples. Although these methods may be useful, conventional glucose sensors continue to exhibit significant analytical bias attributable to the hematocrit effect, generally from about 15 to 30%. Thus, it would be desirable to provide systems for quantifying analytes in biological fluids, in particular the glucose content of whole blood, which reduces bias from the hematocrit effect.

SUMMARY

In one aspect, an electrochemical sensor strip includes a base, first and second electrodes on the base, and a lid on the base. The strip includes at least one first layer on a first conductor, the first layer including a reagent layer including at most 8 μg/mm$^2$ of a mediator. The strip provides a determined concentration value having at least one of a stability bias of less than ±10% after storage at 50° C. for 2 weeks when compared to a comparison strip stored at −20° C. for 2 weeks, a hematocrit bias of less than ±10% for whole blood samples including from 20 to 60% hematocrit, and an intercept to slope ratio of at most 20 mg/dL.

The first and second electrodes of the strip may be in substantially the same plane and the second electrode may include the first layer on a second conductor. The second electrode may include a second layer on the second conductor, and the second layer may include a reagent layer different in composition from the reagent layer of the first layer. The electrodes may be separated by greater than 200 μm and may be separated from an upper portion of the lid by at least 100 μm.

The average initial thickness of the reagent layer of the strip may be less than 8 μm or may be from 0.25 to 3 μm. The reagent layer of the strip may be formed at a deposition density of at most 0.2 μL/mm$^2$ from a reagent solution. The reagent layer may include poly(ethylene oxide), polyvinyl alcohol, hydroxyethylene cellulose, carboxy methyl cellulose, or a combination thereof as a polymeric binder. The deposition density of the polymeric binder may be at most 2 μg/mm$^2$ on the first conductor. The polymeric binder may be partially water soluble and/or may form a gel-like material on hydration.

The reagent layer may include an enzyme system at a deposition density of at most 0.8 μg/mm$^2$ and/or include at most 1.3 Units of enzyme. The reagent layer on the working electrode may include at most 2 μg/mm$^2$ of the mediator. The mediator may be a two electron transfer mediator and may be 3-phenylimino-3H-phenothiazines, 3-phenylimino-3H-phenoxazines, salts thereof, acids thereof, derivatives thereof, or combinations thereof. The mediator may have a redox potential at least 100 mV lower than that of ferricyanide.

The strip may have a stability bias less than ±5% after storage at 50° C. for 2 or 4 weeks when compared a comparison strip stored at −20° C. for 2 or 4 weeks, respectively. The strip may have a hematocrit bias less than ±5% for whole blood samples including from 20 to 60% hematocrit. The strip may have an intercept to slope ratio of at most 10 mg/dL or at most 1 mg/dL.

In another aspect, an electrochemical sensor strip includes a base, first and second electrodes on the base, and a lid on the base. The strip includes at least one first layer on a first conductor, the first layer including a reagent layer including a mediator and an enzyme system, where the reagent layer provides a determined concentration value having at least one of a stability bias of less than ±10% after storage at 50° C. for 2 weeks when compared to a comparison strip stored at −20° C. for 2 weeks, a hematocrit bias of less than ±10% for whole blood samples including from 20 to 60% hematocrit, and an intercept to slope ratio of at most 20 mg/dL.

In another aspect, a method of determining the concentration of an analyte in a sample is provided. The method includes applying a pulse sequence to the sample, the pulse sequence including at least 3 duty cycles within 30 seconds. The method also includes determining the concentration of the analyte in the sample, where the concentration has at least one of a stability bias of less than ±10%, a hematocrit bias of less than ±10% for whole blood samples over a 20 to 60% hematocrit range, and an intercept to slope ratio of at most 20 mg/dL.

The method may include at least 3 duty cycles within 9 seconds and the pulse sequence may be complete in at most 5 seconds. Determining the concentration of the analyte in the sample may include determining the concentration of the analyte in the sample from a current measurement taken within 2 seconds from the application of the pulse sequence. Each duty cycle may include an excitation and a relaxation, where each excitation may have a duration from 0.01 to 3 seconds. The excitations may have a summed duration of at most 10 seconds or at most 2 seconds, and the excitations may have amplitudes differing by 500 mV. The excitations may be at most 45% of the time of the pulse sequence. The relaxations each may have a duration of at least 0.2 seconds or may have a duration of from 0.2 to 3 seconds. The pulse sequence may include an initial excitation from 0.75 to 3 seconds in duration, where this initial excitation is longer in duration than the excitations of the duty cycles.

The method may determine a concentration having a stability bias less than ±5% after storage at 50° C. for 2 or 4 weeks when compared a comparison strip stored at −20° C. for 2 or 4 weeks, respectively. The concentration may have a hematocrit bias less than ±5% for whole blood samples including from 20 to 60% hematocrit. The concentration may have an intercept to slope ratio of at most 10 mg/dL or at most 1 mg/dL.

In another aspect, a method of increasing the performance of quantitative analyte determination includes introducing an analyte containing sample having a liquid component to an electrochemical sensor strip, the strip having a base, a first conductor on the base, a second conductor on the base, and at least one first layer on at least the first conductor, where the at least one first layer includes a reagent layer including a polymeric binder and the sample provides electrical communication between the first and second conductors. The method also includes applying an electric potential between the first and second conductors in the form of at least 4 read pulses within 30 or within 9 seconds and measuring at least one of the read pulses to provide a quantitative value of the analyte concentration in the sample with increased performance attributable to at least one performance parameter selected from a stability bias of less than ±10% after the strip is stored at 50° C. for 2 weeks when compared to a comparison strip stored at −20° C. for 2 weeks, a hematocrit bias of less than ±10% over a 20 to 60% hematocrit range for whole blood samples, an intercept to slope ratio of at most 10 mg/dL, and combinations thereof.

The read pulses may be complete in at most 5 seconds, the read pulses may be measured within 2 seconds of applying the electric potential, and the read pulses may each have a duration of from 0.01 to 3 seconds. The read pulses may have a duration of at most 2 seconds and may be of amplitudes having a difference within 500 mV.

The method may determine the quantitative value having a stability bias less than ±5% after storage at 50° C. for 2 or 4 weeks when compared a comparison strip stored at −20° C. for 2 or 4 weeks, respectively. The method may determine the quantitative value having a hematocrit bias less than ±5% for whole blood samples including from 20 to 60% hematocrit. The method may determine the quantitative value having an intercept to slope ratio of at most 10 mg/dL or at most 1 mg/dL.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like references numerals generally designate corresponding parts throughout the different views.

DETAILED DESCRIPTION

Biosensors provide patients with the benefit of nearly instantaneous measurement of glucose levels. Errors in these measurements may be attributable to a degradation of the reagent composition and/or the hematocrit effect. Degradation of the reagent composition is a continuous process that occurs during the time period that the sensor strip is transported and stored after manufacture. Multiple factors may affect the rate at which the reagent composition degrades, including temperature. The hematocrit effect arises when red blood cells randomly affect the diffusion rate of measurable species to the conductor surface of the working electrode.

By reducing the amount of mediator and/or enzyme used on the sensor strip, the long-term stability of the reagent composition may be increased in relation to conventional biosensors and reagent compositions. Thus, the stability bias and intercept to slope ratios of the sensor strip may be improved. Furthermore, by combining a gated analysis method with the stability-enhanced reagent composition, the hematocrit effect may be reduced. Thus, one or any combination of these and other performance parameters may be improved in accord with the present invention.

In one aspect, the biosensors of the present invention demonstrate a stability bias of preferably less than ±10%, more preferably less than ±5%, after storage at 50° C. for 4 weeks when compared to sensor strips stored at −20° C. for 4 weeks. In another aspect, the biosensors of the present invention demonstrate a hematocrit bias of preferably less than ±10%, more preferably less than ±5% for WB samples including from 20 to 60% hematocrit. In another aspect, the biosensors of the present invention preferably demonstrate an intercept to slope ratio of at most 20 mg/dL, more preferably at most 10 mg/dL or at most 6 mg/dL, and even more preferably at most 1 mg/dL. These and other performance parameters of the sensor strip may be improved.

Figure 1A:
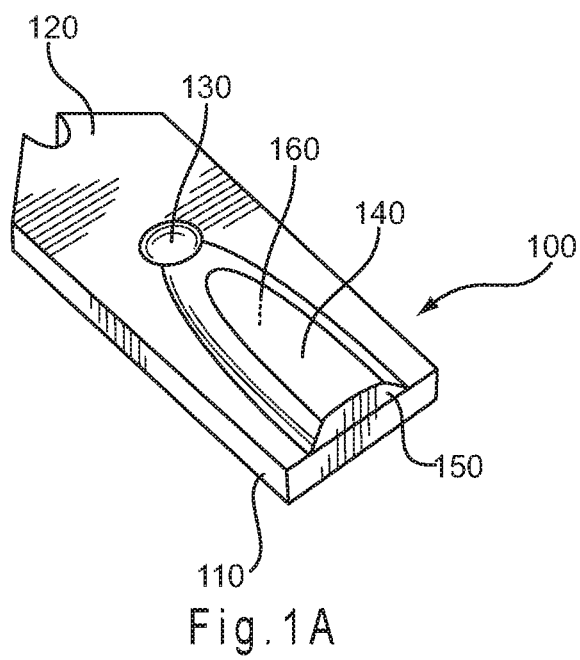
FIG. 1A is a perspective representation of an assembled sensor strip.
Figure 1B:
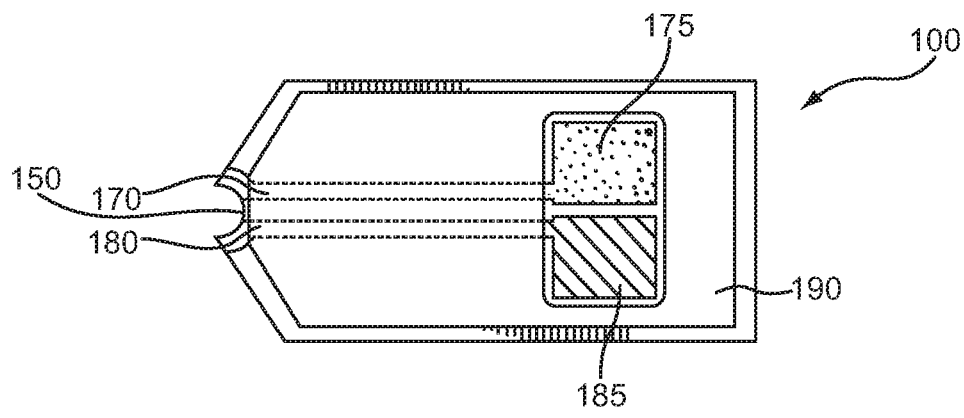
FIG. 1B is a top-view diagram of a sensor strip, with the lid removed.

FIGS. 1A and 1B depict a sensor strip 100, which may be used in the present invention. FIG. 1A is a perspective representation of an assembled sensor strip 100 including a sensor base 110, at least partially covered by a lid 120 that includes a vent 130, a sample coverage area 140, and an input end opening 150. A partially-enclosed volume 160 (the capillary gap or cap-gap) is formed between the base 110 and the lid 120. Other sensor strip designs compatible with the present invention also may be used, such as those described in U.S. Pat. Nos. 5,120,420 and 5,798,031.

A liquid sample for analysis may be transferred into the cap-gap 160 by introducing the liquid to the opening 150. The liquid fills the cap-gap 160 while expelling the previously contained air through the vent 130. The cap-gap 160 may contain a composition (not shown) that assists in retaining the liquid sample in the cap-gap. Examples of such compositions include water-swellable polymers, such as carboxymethyl cellulose and polyethylene glycol; and porous polymer matrices, such as dextran and polyacrylamide.

FIG. 1B depicts a top-view of the sensor strip 100, with the lid 120 removed. Conductors 170 and 180 may run under a dielectric layer 190 from the opening 150 to a working electrode 175 and a counter electrode 185, respectively. In one aspect, the working and counter electrodes 175, 185 may be in substantially the same plane, as depicted in the figure. In a related aspect, the working and counter electrodes 175, 185 may be separated by greater than 200 or 250 μm and may be separated from an upper portion of the lid 120 by at least 100 μm. In another aspect, the working and counter electrodes 175, 185 may be separated by less than 200 μm. The dielectric layer 190 may partially cover the electrodes 175, 185 and may be made from any suitable dielectric material, such as an insulating polymer.

The counter electrode 185 may support the electrochemical activity at the working electrode 175 of the sensor strip 100. In one aspect, the potential to support the electrochemical activity at the working electrode 175 may be provided to the sensor system by forming the counter electrode 185 from an inert material, such as carbon, and including a soluble redox species, such as ferricyanide, within the cap-gap 160. In another aspect, the potential at the counter electrode 185 may be a reference potential achieved by forming the counter electrode 185 from a redox pair, such as Ag/AgCl, to provide a combined reference-counter electrode. Alternatively, the sensor strip 100 may be provided with a third conductor and electrode (not shown) to provide a reference potential to the sensor system.

Figure 2A:
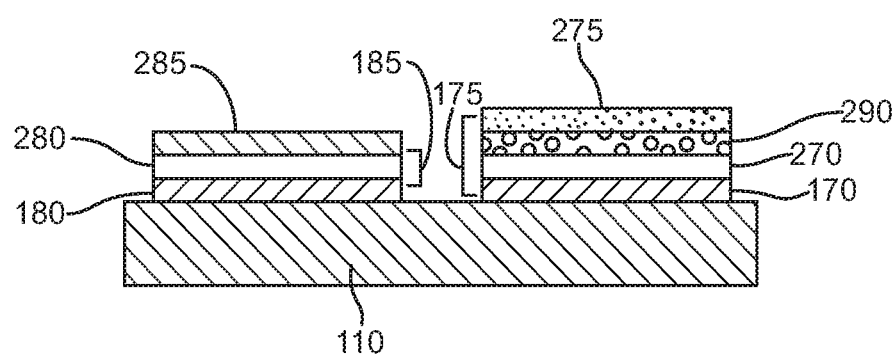
FIG. 2A is an end view diagram of the sensor strip of FIG. 1B.

FIG. 2A depicts an end-view diagram of the sensor strip depicted in FIG. 1B showing the layer structure of the working electrode 175 and the counter electrode 185. The conductors 170 and 180 may lie directly on the base 110.

Surface conductor layers 270 and 280 optionally may be deposited on the conductors 170 and 180, respectively. The surface conductor layers 270, 280 may be made from the same or from different materials.

The material or materials used to form the conductors 170, 180 and the surface conductor layers 270, 280 may include any electrical conductor. Preferable electrical conductors are non-ionizing, such that the material does not undergo a net oxidation or a net reduction during analysis of the sample. The conductors 170, 180 preferably include a thin layer of a metal paste or metal, such as gold, silver, platinum, palladium, copper, or tungsten. The surface conductor layers 270, 280 preferably include carbon, gold, platinum, palladium, or combinations thereof. If a surface conductor layer is not present on a conductor, the conductor is preferably made from a non-ionizing material.

The surface conductor material may be deposited on the conductors 170, 180 by any conventional means compatible with the operation of the sensor strip, including foil deposition, chemical vapor deposition, slurry deposition, and the like. In the case of slurry deposition, the mixture may be applied as an ink to the conductors 170, 180, as described in U.S. Pat. No. 5,798,031.

The reagent layers 275 and 285 may be deposited on the conductors 170 and 180, respectively. The layers are formed from at least one reagent composition that includes reagents and optionally a binder. The binder is preferably a polymeric material that is at least partially water-soluble. In one aspect, the binder may form a gel or gel-like material when hydrated by the sample. In another aspect, the binder may filter red blood cells.

Suitable partially water-soluble polymeric materials for use as the binder may include poly(ethylene oxide) (PEO), carboxy methyl cellulose (CMC), polyvinyl alcohol (PVA), hydroxyethylene cellulose (HEC), hydroxypropyl cellulose (HPC), methyl cellulose, ethyl cellulose, ethyl hydroxyethyl cellulose, carboxymethyl ethyl cellulose, polyvinyl pyrrolidone (PVP), polyamino acids, such as polylysine, polystyrene sulfonate, gelatin, acrylic acid, methacrylic acid, starch, maleic anhydride salts thereof, derivatives thereof, and combinations thereof. Among the above binder materials, PEO, PVA, CMC, and HEC are preferred, with CMC being more preferred at present.

In addition to the binder, the reagent layers 275 and 285 may include the same or different reagents. When including the same reagents, the reagent layers 275 and 285 may be the same layer. In one aspect, the reagents present in the first layer 275 may be selected for use with the working electrode 175, while the reagents present in the second layer 285 may be selected for use with the counter electrode 185. For example, the reagents in the layer 285 may facilitate the free flow of electrons between the sample and the conductor 180. Similarly, the reagents in the layer 275 may facilitate the reaction of the analyte.

The reagent layer 275 may include an enzyme system specific to the analyte that may facilitate the reaction of the analyte while enhancing the specificity of the sensor system to the analyte, especially in complex biological samples. The enzyme system may include one or more enzyme, cofactor, and/or other moiety that participates in the redox reaction with the analyte. For example, an alcohol oxidase can be used to provide a sensor strip that is sensitive to the presence of alcohol in a sample. Such a system could be useful in measuring blood alcohol concentrations. In another example, glucose dehydrogenase or glucose oxidase may be used to provide a sensor strip that is sensitive to the presence of glucose in a sample. This system could be useful in measuring blood glucose concentrations, for example in patients known or suspected to have diabetes.

Enzymes for use in the enzyme system include alcohol dehydrogenase, lactate dehydrogenase, β-hydroxybutyrate dehydrogenase, glucose-6-phosphate dehydrogenase, glucose dehydrogenase, formaldehyde dehydrogenase, malate dehydrogenase, and 3-hydroxysteroid dehydrogenase. Preferable enzyme systems are oxygen independent, thus not substantially oxidized by oxygen.

One such oxygen independent enzyme family is glucose dehydrogenase (GDH). Using different co-enzymes or co-factors, GDH may be mediated in a different manner by different mediators. Depending on their association with GDH, a co-factor, such as flavin adenine dinucleotide (FAD), can be tightly held by the host enzyme, such as in the case of FAD-GDH; or a co-factor, such as Pyrroloquinolinequinone (PQQ), may be covalently linked to the host enzyme, such as with PQQ-GDH. The co-factor in each of these enzyme systems may either be permanently held by the host enzyme or the co-enzyme and the apo-enzyme may be re-constituted before the enzyme system is added to the reagent composition. The co-enzyme also may be independently added to the host enzyme moiety in the reagent composition to assist in the catalytic function of the host enzyme, such as in the cases of nicotinamide adenine dinucleotide NAD/NADH$^+$ or nicotinamide adenine dinucleotide phosphate NADP/NADPH$^+$.

Figure 2B:
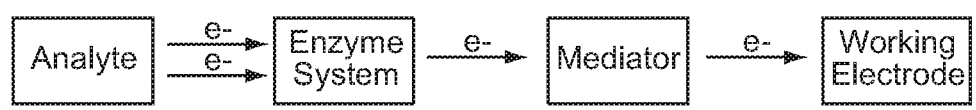
FIG. 2B represents the transfer of a single electron by a mediator from an enzyme system to a working electrode.
Figure 2C:
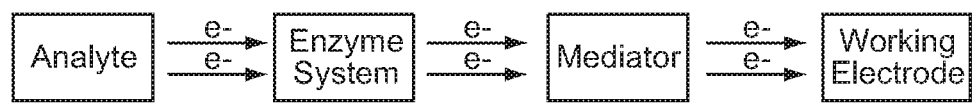
FIG. 2C represents the transfer of two electrons by a mediator from an enzyme system to a working electrode.

The reagent layer 275 also may include a mediator to more effectively communicate the results of the analyte reaction to the surface conductor 270 and/or the conductor 170. Mediators may be separated into two groups based on their electrochemical activity. One electron transfer mediators are chemical moieties capable of taking on one additional electron during the conditions of the electrochemical reaction, while two electron transfer mediators are chemical moieties capable of taking on two additional electrons during the conditions of the reaction. As depicted in FIG. 2B, one electron transfer mediators can transfer one electron from the enzyme to the working electrode, while as depicted in FIG. 2C, two electron transfer mediators can transfer two electrons.

While other mediators may be used, two electron transfer mediators are preferred due to their ability to transfer approximately twice as many electrons from the enzyme system to the working electrode for the same molar amount of mediator in relation to one electron transfer mediators. By reducing the amount of mediator required for the sensor to perform in relation to conventional sensor strips, the sensor strips of the present invention may demonstrate an increase in long-term stability. This stability increase may be attributable to a reduction in enzyme denaturization by the mediator during storage. The stability increase also may be attributable to a reduction in the amount of mediator available to oxidize the enzyme during storage.

Examples of one electron transfer mediators include compounds, such as 1,1'-dimethyl ferrocene, ferrocyanide and ferricyanide, and ruthenium(III) and ruthenium(II) hexaamine. Two electron mediators include the organic quinones and hydroquinones, such as phenathroline quinone; phenothiazine and phenoxazine derivatives; 3-(phenylamino)-3H-phenoxazines; phenothiazines; and 7-hydroxy-9,9-dimethyl-9H-acridin-2-one and its derivatives. Examples of additional two electron mediators include the electro-active organic molecules described in U.S. Pat. Nos. 5,393,615; 5,498,542; and 5,520,786, which are incorporated herein by reference, for example.

Preferred two electron transfer mediators include 3-phenylimino-3H-phenothiazines (PIPT) and 3-phenylimino-3H-phenoxazines (PIPO). More preferred two electron mediators include the carboxylic acid or salt, such as ammonium salts, of phenothiazine derivatives. At present, especially preferred two electron mediators include (E)-2-(3H-phenothiazine-3-ylideneamino)benzene-1,4-disulfonic acid (Structure I), (E)-5-(3H-phenothiazine-3-ylideneamino) isophthalic acid (Structure II), ammonium (E)-3-(3H-phenothiazine-3-ylideneamino)-5-carboxybenzoate (Structure III), and combinations thereof. The structural formulas of these mediators are presented below.

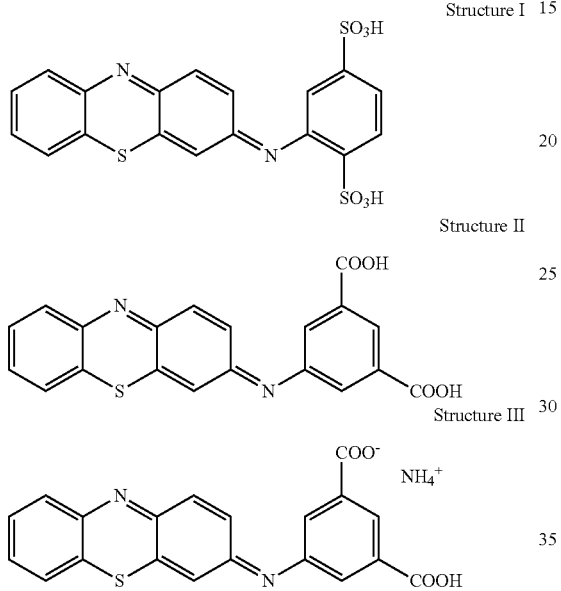

In another respect, preferred two electron mediators have a redox potential that is at least 100 mV lower, more preferably at least 150 mV lower, than ferricyanide.

The reagent layers 275, 285 may be deposited by any convenient means, such as printing, liquid deposition, or ink-jet deposition. In one aspect, the layers are deposited by printing. With other factors being equal, the angle of the printing blade may inversely affect the thickness of the reagent layers. For example, when the blade is moved at an approximately 82° angle to the base 110, the layer may have a thickness of approximately 10 µm. Similarly, when a blade angle of approximately 62° to the base 110 is used, a thicker 30 µm layer may be produced. Thus, lower blade angles may provide thicker reagent layers. In addition to blade angle, other factors, such as the viscosity of the material being applied as well as the screen-size and emulsion combination, may affect the resulting thickness of the reagent layers 275, 285.

When thinner reagent layers are preferred, deposition methods other than printing, such as micro-pipetting, ink jetting, or pin-deposition, may be required. These deposition methods generally give the dry reagent layers at micrometer or sub-micrometer thickness, such as 1-2 µm. For example, pin-deposition methods may provide average reagent layer thicknesses of 1 µm. The thickness of the reagent layer resulting from pin-deposition, for example, may be controlled by the amount of polymer included in the reagent composition, with higher polymer content providing thicker reagent layers. Thinner reagent layers may require shorter pulse widths than thicker reagent layers to maintain the desired measurement performance and/or substantially measure analyte within the diffusion barrier layer (DBL).

The working electrode 175 also may include a DBL that is integral to a reagent layer 275 or that is a distinct layer 290, such as depicted in FIG. 2A. Thus, the DBL may be formed as a combination reagent/DBL on the conductor, as a distinct layer on the conductor, or as a distinct layer on the reagent layer. When the working electrode 175 includes the distinct DBL 290, the reagent layer 275 may or may not reside on the DBL 290. Instead of residing on the DBL 290, the reagent layer 275 may reside on any portion of the sensor strip 100 that allows the reagent to solubilize in the sample. For example, the reagent layer 175 may reside on the base 110 or on the lid 120.

The DBL provides a porous space having an internal volume where a measurable species may reside. The pores of the DBL may be selected so that the measurable species may diffuse into the DBL, while physically larger sample constituents, such as RBCs, are substantially excluded. Although conventional sensor strips have used various materials to filter RBCs from the surface of the working electrode, a DBL provides an internal porous space to contain and isolate a portion of the measurable species from the sample.

When the reagent layer 275 includes a water-soluble binder, any portion of the binder that does not solubilize into the sample prior to the application of an excitation may function as an integral DBL. The average initial thickness of a combination DBL/reagent layer is preferably less than 16 or 8 micrometers (µm) and more preferably less than 4 µm. At present, an especially preferred average initial thicknesses of a combination DBL/reagent layer is from 0.25 to 3 µm or from 0.5 to 2 µm. The desired average initial thickness of a combination DBL/reagent layer may be selected for a specific excitation length on the basis of when the diffusion rate of the measurable species from the DBL to a conductor surface, such as the surface of the conductor 170 or the surface of the surface conductor 270 from FIG. 2A, becomes relatively constant. In one aspect, the DBL/reagent layer may have an average initial thickness of 1 µm or less when combined with an excitation pulse width of 0.25 seconds or less.

The distinct DBL 290 may include any material that provides the desired pore space, while being partially or slowly soluble in the sample. In one aspect, the distinct DBL 290 may include a reagent binder material lacking reagents. The distinct DBL 290 may have an average initial thickness of from 1 to 15 µm, and more preferably from 2 to 5 µm.

Figure 3:
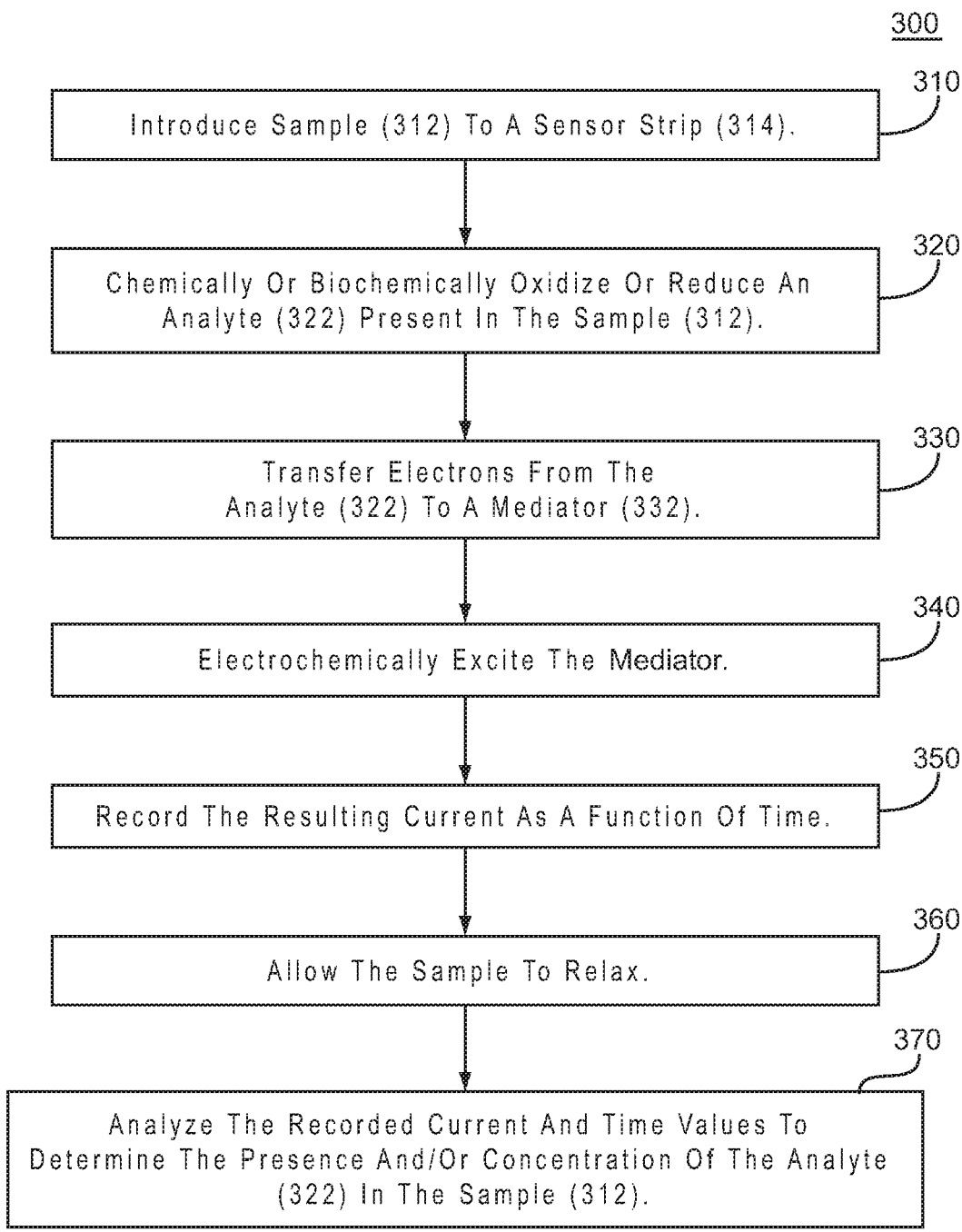
FIG. 3 represents an electrochemical method of determining the presence and concentration of an analyte in a sample.

FIG. 3 represents an electrochemical analysis 300 for determining the presence and optionally the concentration of an analyte 322 in a sample 312. In 310, the sample 312 is introduced to a sensor strip 314, such as the sensor strip depicted in FIGS. 1A-1B and 2A. The reagent layers, such as 275 and/or 285 from FIG. 2A, begin to solubilize into the sample 312, thus allowing reaction. At this point in the analysis, it may be beneficial to provide an initial time delay, or "incubation period," for the reagents to react with the sample 312. Preferably, the initial time delay may be from 0.5 to 5 seconds. A more in-depth treatment of initial time delays may be found in U.S. Pat. Nos. 5,620,579 and 5,653,863.

During the reaction, a portion of the analyte 322 present in the sample 312 is chemically or biochemically oxidized or reduced in 320, such as by an oxidoreductase. Upon oxidation or reduction, electrons may be transferred between the analyte 322 and a mediator 332 in 330, such as through the oxidoreductase.

In 340, the charged mediator 332 is electrochemically excited (oxidized or reduced). For example, when the sample 312 is whole blood containing glucose oxidized by the PQQ-GDH enzyme system in 320, which then transfers two electrons to reduce a phenothiazine derivative mediator in 330, the excitation of 340 oxidizes the phenothiazine derivative mediator at the working electrode. In this manner, electrons are selectively transferred from the glucose analyte to the working electrode of the sensor strip where they may be detected by a measurement device.

The current resulting from the excitation 340 may be recorded during the excitation 340 as a function of time in 350. In 360, the sample undergoes relaxation. Preferably, the current is not recorded during the relaxation 360. The recorded current and time values may be analyzed to determine the presence and/or concentration of the analyte 322 in the sample 312 in 370.

Amperometric sensor systems apply a potential (voltage) to the sensor strip to excite the measurable species while the current (amperage) is monitored. Conventional amperometric sensor systems may maintain the potential while measuring the current for a continuous read pulse length of from 5 to 10 seconds, for example. In contrast to conventional methods, the duty cycles used in the electrochemical analysis 300 replace continuous, long-duration read pulses with multiple excitations and relaxations of short duration. A more detailed description of multiple excitation and relaxation or "gated" pulse sequences may be found in PCT/US2006/028013, filed Jul. 19, 2006, entitled "Gated Amperometry."

Referring to FIG. 3, the excitation 340, the recordation 350, and the relaxation 360 constitute a single duty cycle. Preferably, at least 2, 4, 6, or 7 duty cycles are applied during an independently selected 3, 5, 7, 9, or 14 second time period. In one aspect, the duty cycles are applied during a 3 to 14 second time period. In another aspect, at least 4 duty cycles are applied within 30 seconds, 9 seconds, or less. In another aspect, from 2 to 6 duty cycles may be applied within 10 seconds or less. In another aspect, from 2 to 4 duty cycles may be applied within 3 to 9 seconds.

After the excitation 340, in 360 the measurement device may open the circuit through the sensor strip 314, thus allowing the system to relax. During the relaxation 360, the current present during the excitation 340 is substantially reduced by at least one-half, preferably by an order of magnitude, and more preferably to zero. Preferably, a zero current state is provided by an open circuit or other method known to those of ordinary skill in the art to provide a substantially zero current flow. In one aspect, the relaxation 360 is at least 0.5 or at least 0.2 seconds in duration. In another aspect, the relaxation 360 is from 0.2 to 3 seconds or from 0.5 to 1 second in duration.

FIGS. 4A-4D depict examples of gated amperometric pulse sequences where multiple duty cycles were applied to the sensor strip after introduction of the sample. In these examples, square-wave pulses were used; however, other wave types compatible with the sensor system and the test sample also may be used.

Each depicted pulse sequence includes an initial one second excitation pulse 420 followed by multiple 0.25 second excitations 430. The initial excitation pulse 420 may be of longer duration than the subsequent excitations 430. For example, the initial excitation pulse 420 may range from 0.75 to 3 seconds in duration. The length of the excitation pulse 420 may be tailored to oxidize the relatively small amount of enzyme system deposited on the strip. When the initial excitation pulse 420 is used, it is preferably of longer duration than the following multiple excitations 430. For example, the pulse sequence may include the initial excitation pulse 420 having a duration of 2 seconds, followed by an open circuit relaxation of 3 seconds, followed by the subsequent excitation 430 having a duration of 0.125 seconds.

Figure 4A:
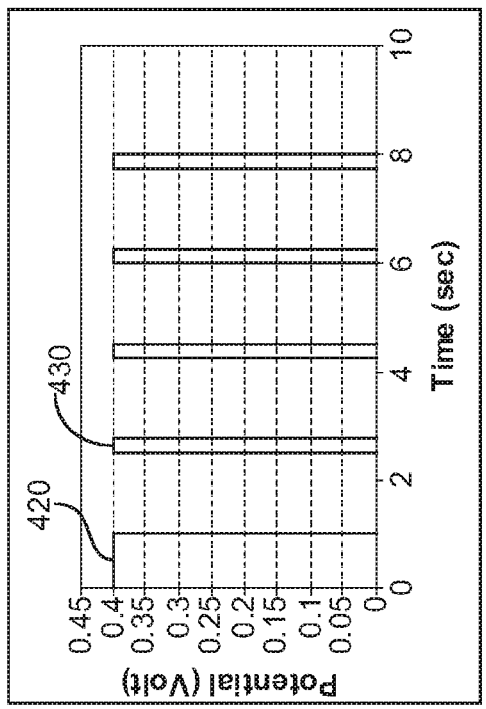
FIGS. 4A-4D depict examples of gated amperometric pulse sequences where multiple duty cycles were applied to the sensor strip after introduction of the sample.
Figure 4B:
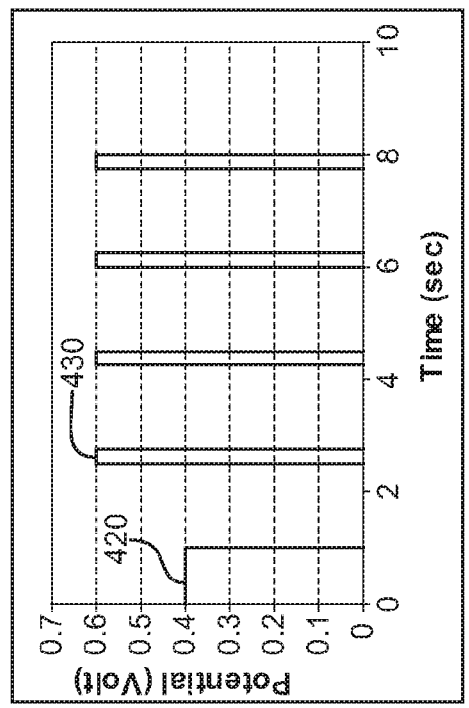
Figure 4C:
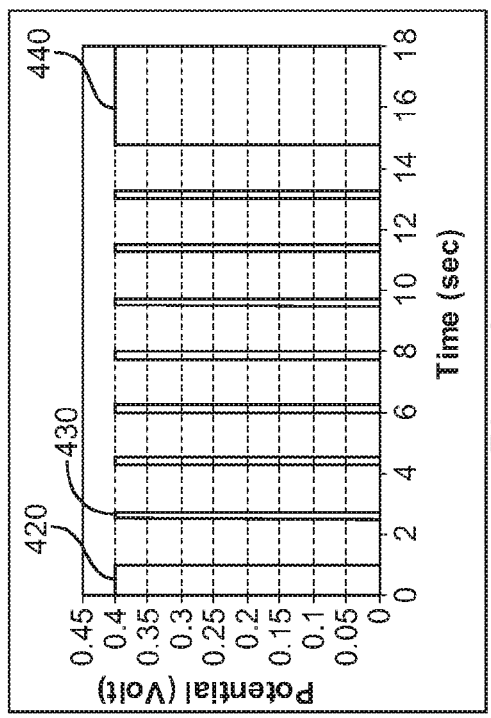
Figure 4D:
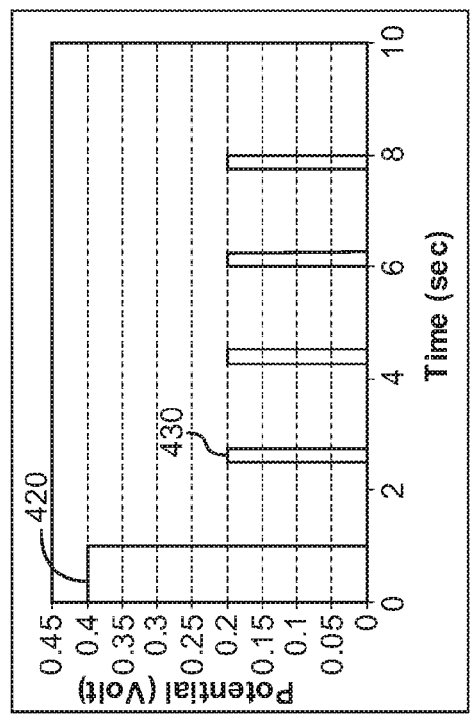

The multiple excitations 430 may range from 0.01 to 3 seconds in duration. In one aspect, the total excitation length is two seconds or less, thus including the initial one second pulse 420 followed by four of the 0.25 second excitations 430. In another aspect, the total excitation length is 1.5 seconds or less, thus including the initial one second pulse 420 followed by one or two of the 0.25 second excitations 430. The pulse sequence may include additional excitations, such as excitation 440 depicted in FIG. 4A. In another aspect, the excitations may be of different amplitudes, such as depicted in FIGS. 4C and 4D. In a preferred aspect, when excitations of different amplitudes are used, the difference in amplitudes may be within 500 mV.

The short excitations may permit the accurate analysis of the sample with reagent compositions having reduced polymer, enzyme system, and mediator concentrations in relation to conventional compositions. Furthermore, the short excitations allow for the analysis to be completed within 8.5 seconds or less, or more preferably, 5 seconds or less from the initial application of a signal to the sensor strip.

Either short or long excitations may be used. Preferably, the current measurement that the analyte concentration is determined from is taken within 2 seconds or 1 second of the initial application of the signal. More preferably, multiple short excitations are combined with a current measurement taken within 2 seconds, 1 second, or less from the initial application of the signal to determine the analyte concentration of the sample.

In combination with the gated amperometric pulse sequences of the present invention, reagent compositions including specific amounts of polymeric binder, enzyme system, and/or mediator were found to reduce hematocrit bias and/or increase long-term stability. While conventional strips are often described in terms of the percent of each reagent composition ingredient, it is the density of each reagent composition ingredient (absolute amount per area) that is relevant to long-term stability. By limiting the amount of mediator and enzyme available for interaction, the amount of environmentally reduced mediator (mediator not responsive to the underlying analyte concentration) present at the time of analysis may be substantially reduced. Thus, providing a beneficial reduction in background current. As conventional biosensors use excess enzyme in an attempt to improve long-term stability, it was unexpected that a reduction in the enzyme system and/or mediator provided an improvement in long-term stability for the present biosensors. Furthermore, if individual reagent compositions are optimized for each electrode, the relative amount of mediator available to interact with the enzyme may be further reduced in relation to single reagent composition sensor strips.

For example, hematocrit biases were larger with the higher polymer concentrations of 2%, 1.5%, and 1% than with a 0.5% (w/w) polymer concentration in the reagent solution when using high enzyme loading. This may be attributable to higher polymer concentrations producing thicker reagent layers that affect hematocrit bias on re-hydration. Thus, as assay times become shorter, rapid re-hydration without an increase in hematocrit bias may be preferred. In this manner, a preferable balance may be reached between the polymer content and enzyme loading of the reagent composition to provide the desired level of hydration during the time of the assay. When applied to the sensor strip, polymer deposition densities of 2 μg/mm² or less may be preferred, with polymer deposition densities from 0.8 to 1.5 μg/mm² being more preferred.

When different deposition solutions are deposited on the working and counter electrodes, the amount of the enzyme system present on the working electrode is controlling. Thus, depositing approximately 0.24 μL of a solution including 1.2 U of the PQQ-GDH enzyme system, 2.57 μg of the Structure I mediator, 1.18 μg of the CMC polymer, and 3.28 μg of phosphate buffer provides a reagent solution concentration of 5 U/μL enzyme system, 24 mM mediator, 0.5% polymer, and 100 mM phosphate buffer.

Depositing this reagent solution on a deposition area of 1.5 mm² including a working electrode area of 1 mm², provides an enzyme system deposition density at the working electrode of about 0.8 U/mm² (1.2 U/1.5 mm²), a mediator deposition density of 1.72 μg/mm² (2.57 μg/1.5 mm²), a polymer deposition density of 0.8 μg/mm², and a phosphate buffer deposition density of 2.2 μg/mm². Similarly, for a reagent solution including approximately 2 U/μL of the PQQ-GDH enzyme system, 24 mM of the Structure I mediator, 0.5% CMC, and 100 mM phosphate buffer, the enzyme system deposition density will be about 0.3 U/mm². Furthermore, the specific activity of an enzyme system may be translated into weight density in terms of μg/mm². For example, if the activity of an enzyme system is 770 U/mg, the enzyme system's activity density of 0.3 U/mm² becomes 0.39 μg/mm² in weight density. Thus, the activity of an enzyme system may be taken into account when determining the deposition density for the enzyme system.

Conventional reagent layers include enzyme deposition densities of 1 to 6 μg/mm². In contrast, after deposition, reagent compositions of the present invention may include enzyme system deposition densities of less than 1 μg/mm², preferably less than 0.5 μg/mm². The deposition solutions of the present invention may include about 4 U/μL or less of the enzyme system or may include about 3 U/μL or less of the enzyme system. At present, 2.2 U/μL or less of the PQQ-GDH enzyme system may be included in the reagent solution. Thus, when the reagent composition is applied to the sensor strip, 1.3 Units or less of the enzyme system may be present on the sensor strip, with from 0.3 to 0.8 Units being more preferred.

Conventional sensor strips generally have mediator deposition densities ranging from 10 to 25 μg/mm². In contrast, mediator deposition densities of 8 μg/mm² and less are preferred for the present invention, with mediator deposition densities of 5 μg/mm² and less being more preferred. At present, mediator deposition densities of 2 μg/mm² and less are especially preferred. In a preferred aspect, two electron mediators are preferable to one electron mediators.

Table I, below, provides the deposition densities of the polymeric binder, buffer, enzyme system, and mediator components in the reagent compositions used in FIGS. 5A-5E and FIGS. 6A-6C, discussed below. The enzyme system deposition density for reagent composition 3 (RC3) at 0.42 μg/mm² is nearly 60% less than the lowest 1 μg/mm² value of the previously discussed conventional strips.

Similarly, the mediator densities given in Table I are approximately one order of magnitude smaller than those of conventional sensor strips. For example, the mediator deposition density of RC3 was approximately one-fifth that of a conventional sensor strip. This reduction in the deposition density of the mediator in relation to conventional sensor strips may provide a substantial increase in the long-term stability of the reagent compositions of the present invention.

TABLE I

| | CMC, μg/mm² | Buffer, μg/mm² | PQQ/GDH, μg/mm² | Mediator, μg/mm² |
|---|---|---|---|---|
| RC1 | 1.59 | 2.17 | 3.99 | 1.72 |
| RC2 | 0.79 | 2.19 | 1.07 | 1.72 |
| RC3 | 0.79 | 2.19 | 0.42 | 1.72 |
| RC4 | 0.77 | 2.22 | 0.99 | 1.36 |

Figure 5A:
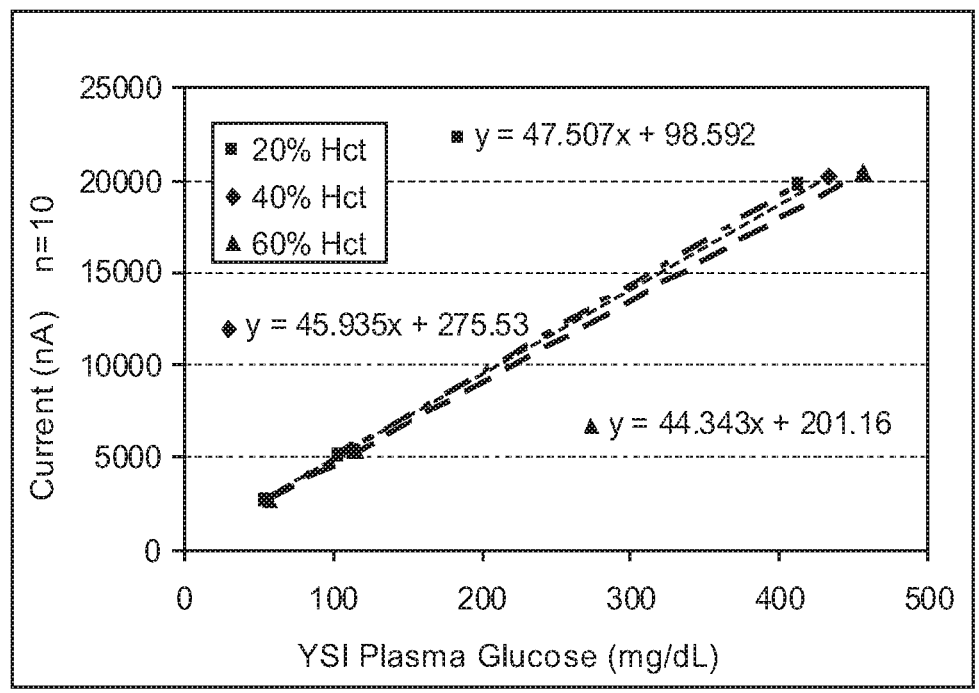
FIGS. 5A and 5B depict the dose response curves for sensor strips including the PQQ-GDH enzyme system at the 20%, 40% and 55% hematocrit level.
Figure 5B:
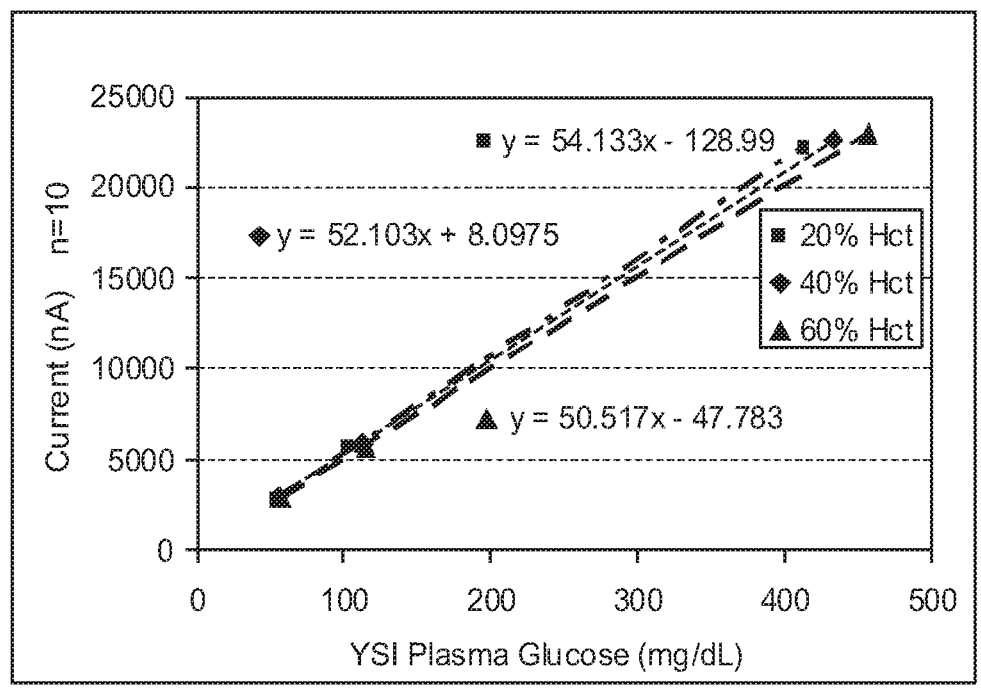

FIG. 5A depicts the glucose dose response curves at different hematocrit levels in WB samples for the RC2 sensor strip that included 1.2 unit per sensor (U/sensor) at a deposition density of 0.8 U/mm² of the PQQ-GDH enzyme. FIG. 5B depicts the glucose dose response curves at different hematocrit levels in WB samples for the RC3 sensor strip that included 0.5 U/sensor at a deposition density of 0.3 U/mm² of the PQQ-GDH enzyme. Both the 1.2 U and 0.5 U sensors delivered hematocrit biases less than ±5%. However, a difference between the 1.2 U and 0.5 U sensors was observed with regard to the system sensitivity and intercept.

A reduction in the ratio of intercept-to-slope may be seen for the 0.5 U/sensor of FIG. 5B by comparing the intercept to slope (I/S) ratios, expressed in units of mg/dL, with those of the 1.2 U/sensor of FIG. 5A, with lower ratios representing a reduction in background signal. Thus, the I/S ratio for the 1.2 U/sensor of FIG. 5A is ~6 mg/dL, while the I/S ratio for the 0.5 U/sensor of FIG. 5B is ~0.15 mg/dL, an approximate 40 time reduction at the 40% hematocrit concentration. The superior background signal performance of the 0.5 U sensor in relation to a 1.5 U sensor was established.

In one aspect, the performance characteristic of low background (low intercept) may be provided by relatively low mediator and enzyme deposition densities. In another aspect, the performance characteristic of high sensitivity (high slope) may be provided by optimizing the timing ratio of the excitations and relaxations of the pulse sequence. For example, combining a relatively long relaxation period of 1.5 seconds with a relatively short excitation period of 0.25 second provides a large current density at the surface of the working electrode. Numerically, the relatively small intercept value over the relatively large slope value further improves the I/S. Thus, preferable sensor performance characteristics (small I/S values) may be provided by the reagent composition and the measurement method in combination.

Equation (1), below, provides an analytical relationship between the current imprecision and the resulting imprecision in the determined glucose concentration as a function of the I/S ratio when the glucose and current relationship is $i = S*G + Int$:

$$\frac{\Delta G/G}{\Delta i/i} = \frac{SD_G/G}{SD_i/i} = \frac{\% \ CV_G}{\% \ CV_i} = 1 + \frac{1}{G}\frac{Int}{S}, \quad (1)$$

where G denotes the glucose concentration, $\Delta G/G$ is the relative error of the glucose concentration in mg/dL, $\Delta i/i$ is the relative error of the measured current, $SD_G/G$ is the relative standard deviation in $\Delta G/G$, $SD_i/i$ is the relative standard deviation in $\Delta i/i$, % $CV_G$ is the coefficient of variance, which is proportional to relative standard deviation and represents the glucose measurement precision, %$CV_i$ is the coefficient of variance, which is proportional to relative standard deviation and represents the current measurement precision, and Int/S is the intercept-to-slope (I/S) ratio in mg/dL. Equation (1) may be derived from i=S*G+Int by taking the derivative of the reverse function G=f(i)=(i−Int)/S in the derivation and analysis of error propagation. Due to the 1+I/G term, a current imprecision of 1 results in a glucose concentration imprecision of greater than 1 if the I/S value is greater than zero. Intercept to slope (I/S) ratios expressed in mg/dL may be expressed in terms of millimoles/Liter (mM/L) by dividing the I/S (mg/dL) value by 18 ([mg/dL]/18=[mM] for glucose).

Current imprecision describes the variance between the current measurements of multiple sensor strips. Thus, current imprecision represents the amount that a recorded current value differs from the mean current value when identical glucose samples are analyzed using multiple sensor strips. The more a recorded current value from a particular strip deviates from the mean value for multiple strips, the poorer the current recorded from that strip correlates with the actual glucose concentration of the sample. Thus, the current measurement precision may measured by its imprecision or %-$CV_i$, and the glucose measurement precision also may be measured by its imprecision or %-$CV_G$.

Table II, below, provides slopes (1/G values) calculated with Equation (1) from multiple glucose concentrations in mg/dL. Thus, 1/57.6=0.0174, 1/111=0.009, 1/222.25=0.0045, 1/444.75=0.0022, and 1/669=0.0015, where the denominators are the plasma glucose concentrations tested. As the glucose concentration increases, the slope value decreases according to equation (1).

TABLE II

| Glucose Concentration in mg/dL | I/S Ratio Calculated from Equation (1) | Experimentally Determined I/S Ratio |
| --- | --- | --- |
| 57.6 | 0.0174 | 0.0174 |
| 111 | 0.009 | 0.009 |
| 222.25 | 0.0045 | 0.0045 |
| 444.75 | 0.0022 | 0.0022 |
| 669 | 0.0015 | 0.0015 |

Figure 5C:
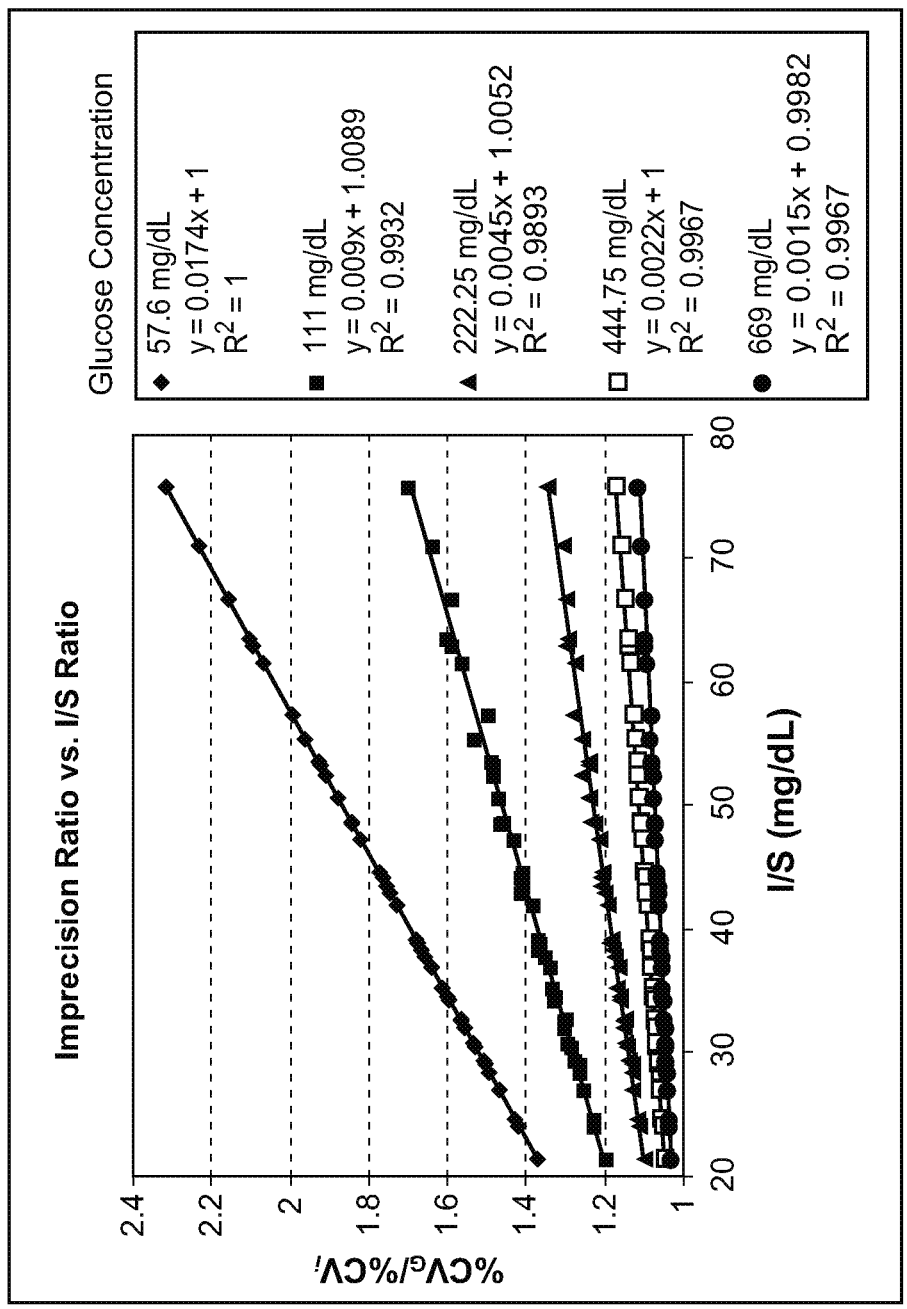
FIG. 5C presents I/S ratios in mg/dL determined from experimental data.

FIG. 5C presents I/S ratios in mg/dL determined from experimental data. The current values were obtained with gated amperometric pulse sequences from WB samples including 40% hematocrit and glucose concentrations of 57.6, 111, 222.25, 444.75, or 669 mg/dL. Calibration constants were determined at 4, 5.5, 7, 8.5, 10, 11.5, 13, and 14.5 seconds into the analysis. As can be seen from the table, the calculated and experimentally determined values are the same, confirming the ability of Equation (1) to describe the behavior of the sensor strip regarding glucose and current imprecision.

For low glucose concentrations, such as 50 mg/dL and below, it is preferable to maintain a low I/S value to reduce the imprecision introduced into the determined glucose concentration from the underlying imprecision in the recorded current value. For example, if the I/S ratio is 50 mg/dL and the glucose concentration is 50 mg/dL, then the ratio of %-$CV_G$/%-$CV_i$ is 2 [1+(I/S)/G=1+50/50=2], and any current imprecision will be amplified by a factor of 2 in the determined glucose concentration. Thus, if the typical imprecision in the recorded current values is 3.5%, a system having an I/S ratio of 50 mg/dL results in a glucose imprecision of 7%.

Figure 5D:
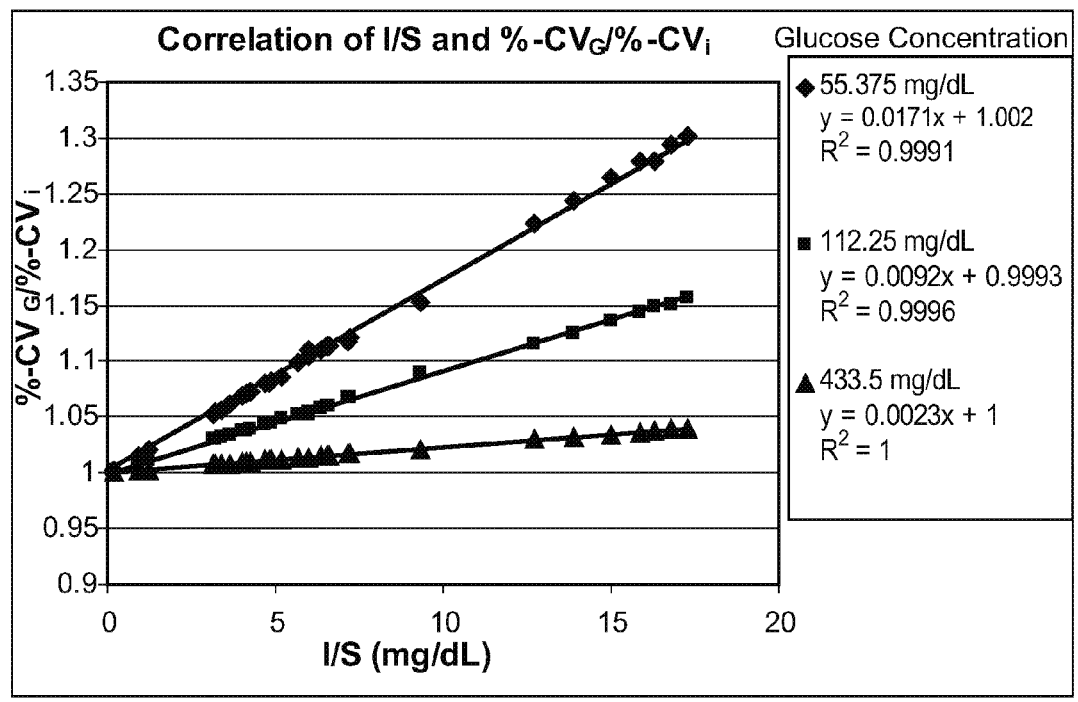
FIG. 5D shows I/S ratios from 0 to 20 mg/dL for multiple glucose concentrations determined from sensor strips having reagent compositions RC2, RC3, or RC4.

FIG. 5D shows I/S ratios from 0 to 20 mg/dL for glucose concentrations of 55.375, 112.25, and 433.5 mg/dL determined from sensor strips having reagent compositions RC2, RC3, or RC4 from Table I, above. As the I/S ratios decrease from 20, the imprecision associated with the determined glucose concentration also decrease. Thus, demonstrating that lower I/S ratios are preferred at lower glucose concentrations, as previously discussed.

When each of these factors are considered, sensor strips having an I/S ratio of 20 mg/dL or less are preferred, with those having I/S ratios of 10 mg/dL or less or 6 mg/dL or less being more preferred. At present, strips having an I/S ratio of 1 mg/dL or less are even more preferred.

Figure 5E:
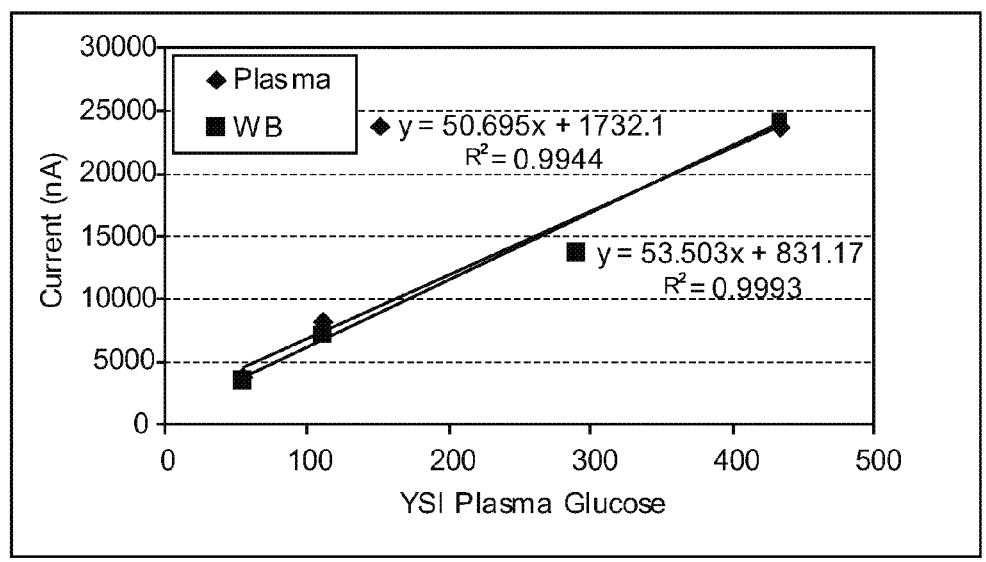
FIG. 5E shows the nearly identical hematocrit performance of the system with plasma and 40% hematocrit whole blood samples.

FIG. 5E shows the nearly identical hematocrit performance of a sensor system in accord with the present invention used with plasma and 40% hematocrit whole blood samples. In this example, the reagent composition of the sensor strip was RC2, as described in Table I, above. Thus, the gated pulse sequences in combination with the reagent compositions of the present invention provide a substantial reduction in the hematocrit effect observed for WB samples.

Figure 6A:
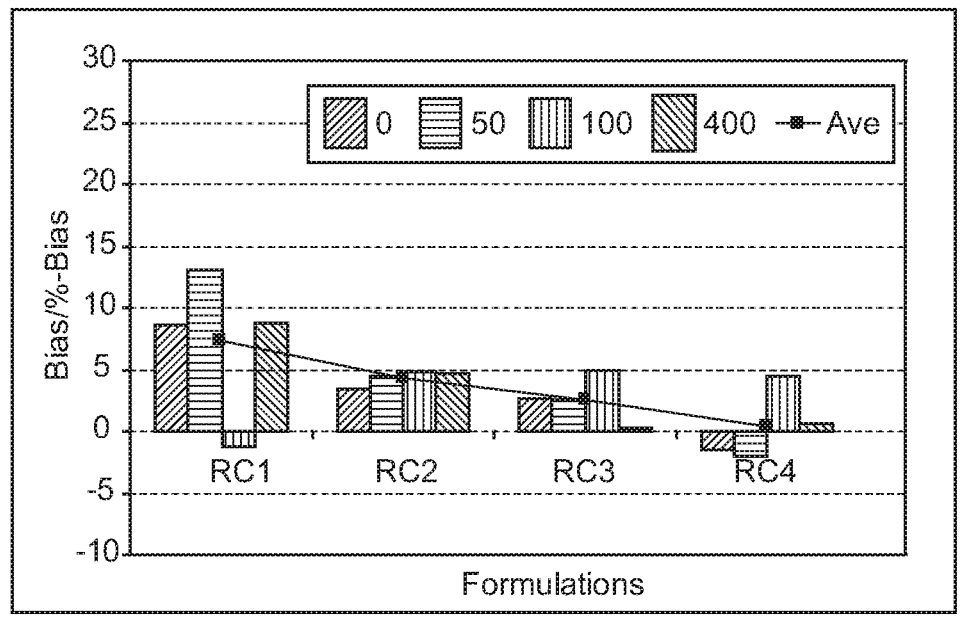
FIG. 6A shows the stability bias for four reagent compositions including the PQQ-GDH enzyme system after 2 weeks at 50° C.

FIG. 6A shows the effect of environmental stress on the long-term stability of sensor strips. The Y-axis of the graph shows the absolute stability bias in terms of mg/dL for glucose concentrations below 75 mg/dL or the %-bias for glucose concentrations at and above 75 mg/dL for environmentally stressed sensor strips in relation to sensor strips stored at −20° C. The stressed sensor strips had been stored at 50° C. for two weeks as an accelerated process simulating storage at 25° C. for 18 months. Since the mediator density was initially low (1.72 ug/mm$^2$), the average stability bias line in FIG. 6A established that as the enzyme density decreased from RC1 (3.2 U/mm$^2$, or 4 ug/mm$^2$ at 770 U/mg specific enzyme activity) to RC2, RC3 and RC4 (both at 0.8 U/mm$^2$ or less), so did the environmentally induced biases.

FIG. 6A also established that a reagent composition in accord with the present invention may provide long-term stability sufficient to not require an initial long oxidative pulse before the analysis, such as that described in U.S. Pat. No. 5,653,863 to Genshaw et al. The analysis that generated the data of FIG. 6A had a total duration of 4.5 seconds with a total oxidation time of 1.5 seconds (corresponding to pulse sequence of FIG. 4A). Thus, only 30% of the assay time was spent oxidizing the WB sample in FIG. 6A, compared to ~67% of the total assay time in the U.S. Pat. No. 5,653,863 analysis (20 seconds of oxidation over a 30 second total analysis time). In one aspect, 45% or less of the total assay time is spent oxidizing the sample. In another aspect, 35% or less of the total assay time is spent oxidizing the sample.

While the Structure III mediator appeared to have a slightly lower stability bias than the Structure I mediator in FIG. 6A, this small difference may be attributable to other factors within the test system. Thus, reagent compositions RC2, RC3, and RC4 in combination with the gated pulse sequences of the present invention demonstrated a stability bias of less than ±5% after exposure to 50° C. temperatures for two weeks, while RC1 with a higher enzyme system deposition density did not.

Figure 6B:
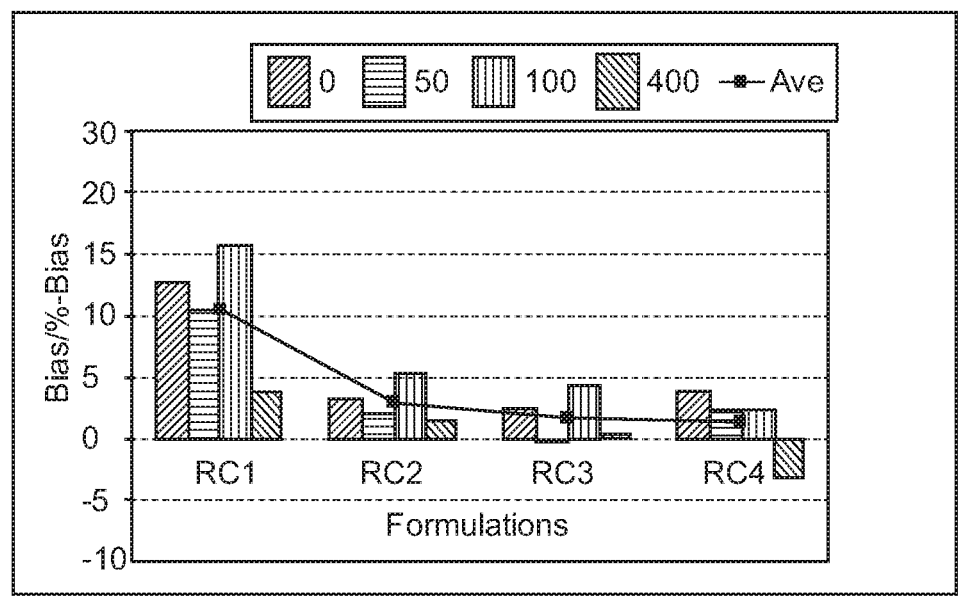
FIG. 6B shows the stability bias for four reagent compositions including the PQQ-GDH enzyme system after 4 weeks at 50° C.

FIG. 6B shows the effect of environmental stress on the long-term stability of sensor strips stored at 50° C. for four weeks. The Y-axis of the graph shows the absolute stability bias in terms of mg/dL for glucose concentrations below 75 mg/dL or the %-bias for glucose concentrations at and above 75 mg/dL for environmentally stressed sensor strips in relation to sensor strips stored at −20° C. The increase in stability bias for the 4 week storage period of FIG. 6B in relation to the shorter 2 week storage period of FIG. 6A is seen in the Y-axis values for RC1. Since the mediator density was initially low (1.72 ug/mm$^2$), the average stability bias line in FIG. 6B established that as the enzyme density decreased from RC1 (3.2 U/mm$^2$, or 4 ug/mm$^2$ at 770 U/mg specific enzyme activity) to RC2, RC3, and RC4 (both at 0.8 U/mm$^2$ or less), so did the environmentally induced biases. Thus, the average stability bias line for the longer 4 week storage period of FIG. 6B also decreases substantially for RC2, RC3, and RC4 in relation to RC1. Even after 4 weeks of storage at 50° C., reagent compositions RC2, RC3, and RC4 in combination with the gated pulse sequences of the present invention demonstrated a stability bias of less than ±5%.

Figure 6C:
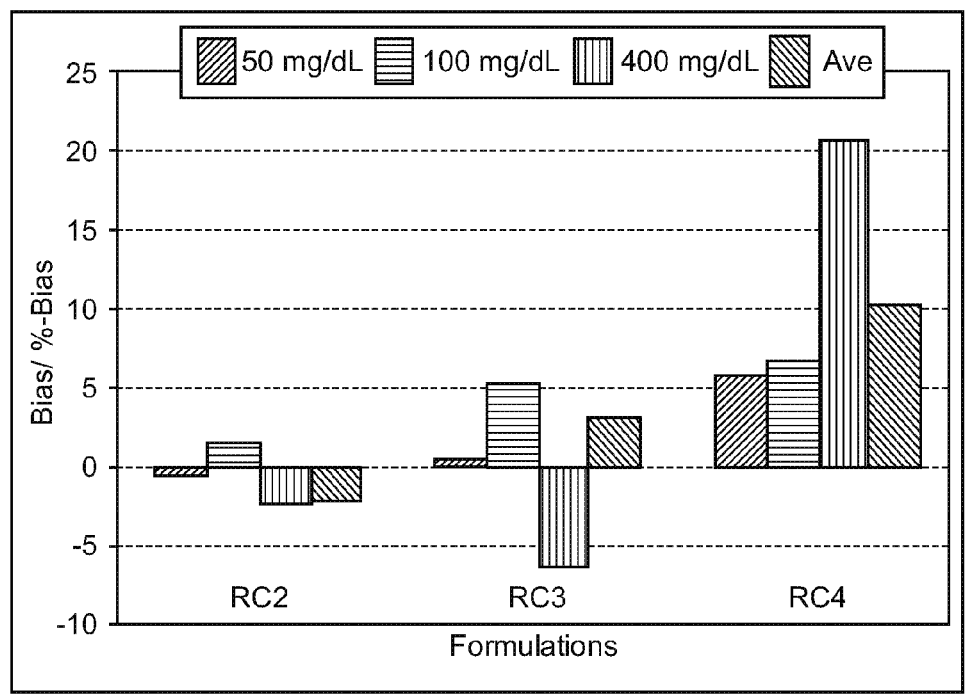
FIG. 6C shows the stability bias for three reagent compositions including the PQQ-GDH enzyme system after 52 weeks at 25° C. under 80% relative humidity.

FIG. 6C shows the stability bias for three reagent compositions including the PQQ-GDH enzyme system after 52 weeks at 25° C. under 60% relative humidity. Unlike in FIGS. 6A and 6B a longer time period at a lower temperature was used to age the strips. The bias values for RC2 and RC3 were similar to those observed under accelerated aging, being less than ±5% on average. RC4 showed an increase in bias in relation to the accelerated aging results of FIGS. 6A and 6B, increasing to a bit less than the ±10% level on average. This increase may be attributable to experimental error or to a stability issue with the lot of Structure III mediator used in RC4 under the specific circumstances of this test.

Figure 6D:
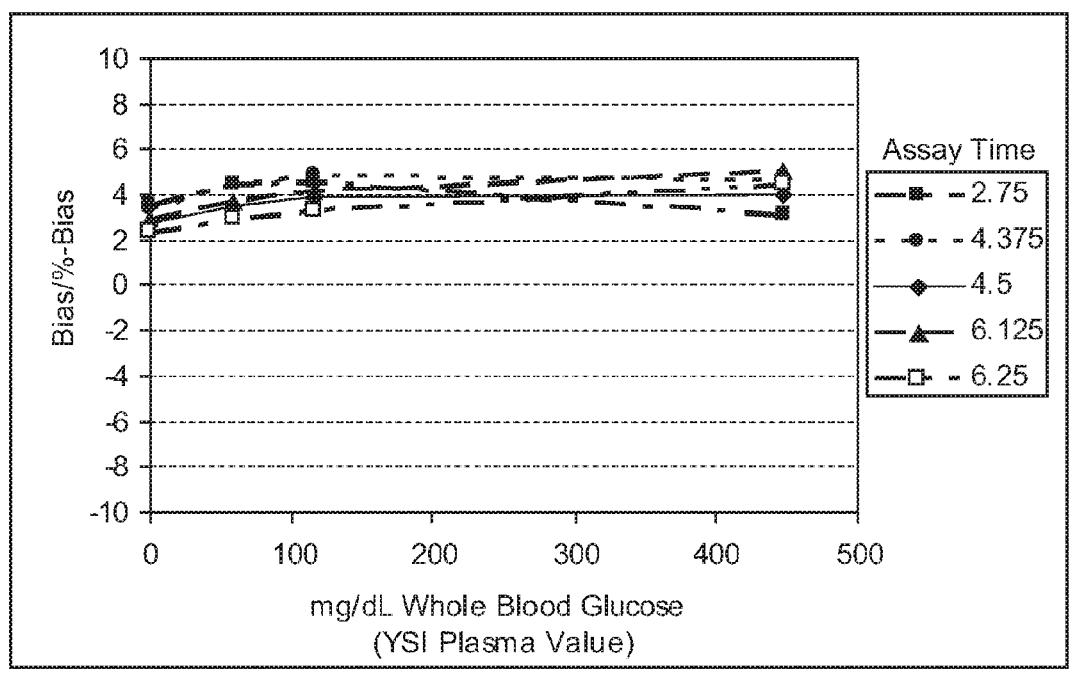
FIG. 6D shows the variance in stability bias for sensor strips including RC2 where the data point used to calculate the analyte concentration was taken at varying times after starting the analysis.

FIG. 6D shows the stability bias values for sensor strips including RC2 where the data point used to calculate the analyte concentration was taken at a specific time after starting the analysis. For example, the 2.75 second line represents the bias/%-bias values of analyte concentration as determined after the first short excitation pulse, such as the excitation 430 in FIG. 4A. Similarly, the 4.375 second line represents the bias/%-bias values of analyte concentration as determined after a second short excitation pulse. Thus, using an environmentally stressed sensor strip including RC2 and a gated pulse sequence, the analyte concentration of the sample may be accurately determined in less than 3 seconds.

Example 1

Sensor Strip Preparation

In one aspect, sensor strips in accord with the present invention were made using pin-deposition. The counter electrode reagent solution was prepared by making a stock solution of 100 mM phosphate buffer in 1% carboxylmethyl cellulose (CMC). Then, enough powdered mediator was dissolved into the buffer/CMC solution to make a final solution of 100 mM mediator in 100 mM phosphate buffer and 1% CMC.

The working electrode reagent solution was prepared typically by making a stock solution of 100 mM phosphate buffer in 0.5% CMC (100 mL for example). Then, enough powdered mediator was dissolved into the buffer/CMC stock solution to make a solution (10 mL for example) of 24-25 mM mediator in 100 mM phosphate buffer and 0.5% CMC. Finally, for an enzyme loading of 5 U/µL, about 33.4 mg of the PQQ-GDH enzyme system (749 U/mg specific activity) was combined with 5 mL of the mediator/buffer/CMC solution in a glass container ([5000 U/mL*5 mL]/[749 U/mg]=33.4 mg). The mixture was slowly swirled to dissolve the dry enzyme powder into the solution. This formulation was for RC2. If only 2 mL of final reagent solution was needed, then about 13.4 mg PQQ-GDH enzyme with 749 U/mg specific activity was weighed out. Similarly for RC3 composition of 2 U/µL, about 13.4 mg of PQQ-GDH enzyme with the specific activity of 749 U/mg was dissolved by 5 mL of the mediator/buffer/CMC solution to make up the final reagent solution for deposition. If only 2 mL of the final reagent solution was needed, then about 5.34 mg PQQ-GDH enzyme at 749 U/mg specific activity was weighed out to make the final solution.

Pin-deposition was used to deposit the counter electrode reagent solution on one of the carbon surfaces to form the counter electrode. The volume delivered by each deposition was from about 0.2 to 0.24 µL, which spread to cover an area of about 1.5 to 2 mm$^2$. Similarly, pin-deposition was used to deposit the working electrode reagent solution on one of the carbon surfaces to form the working electrode. The volume for each working electrode deposition was also about 0.2-0.24 µL with a similar solution spread over the carbon to form the working electrode. The completed sensor sheet was allowed to air-dry for 15 minutes followed by storage in a desiccated container before final lamination to form the completed sensor strips. In one aspect, reagent solution deposition densities of 0.16 µL/mm$^2$ (0.24 uL/1.5 mm$^2$) or less at the working electrode are preferred.

Example 2

Donor Study

Whole blood samples were collected from 21 subjects having diabetes mellitus. Two analyses were performed on each subject to provide 42 measurements from each of the four sensor strip lots SS1 through SS4 as provided in Table III, below. Different working and counter electrode reagent compositions were used for SS1 through SS3, while SS4 used a single reagent composition substantially covering both conductors. SS1, SS2, and SS3 represent different manufacturing lots using the same reagent amounts. The volume of reagent composition deposited on the individual conductors for SS1 through SS3 was about 0.24 µL, with two deposition areas of about 1.5 mm$^2$ each. The volume of reagent composition deposited to cover both conductors for SS1 was about 0.3 µL, with a total deposition area of about 3 mm$^2$.

TABLE III

| | Working Electrode Deposition | Counter Electrode Deposition |
|---|---|---|
| SS1 | 1.62 µg/mm$^2$ CMC<br>1.11 µg/mm$^2$ Buffer<br>0.58 µg/mm$^2$ PQQ/GDH Enzyme System<br>1.39 µg/mm$^2$ Structure I Mediator<br>pH 7.2 ± 0.1 | 1.62 µg/mm$^2$ CMC<br>1.11 µg/mm$^2$ Buffer<br>1.39 µg/mm$^2$ Structure I Mediator<br>pH 7.2 ± 0.1 |
| SS2 | 1.62 µg/mm$^2$ CMC<br>1.11 µg/mm$^2$ Buffer<br>0.58 µg/mm$^2$ PQQ/GDH Enzyme System<br>1.39 µg/mm$^2$ Structure I Mediator<br>pH 7.2 ± 0.1 | 1.62 µg/mm$^2$ CMC<br>1.11 µg/mm$^2$ Buffer<br>1.39 µg/mm$^2$ Structure I Mediator<br>pH 7.2 ± 0.1 |

TABLE III-continued

| | Working Electrode Deposition | Counter Electrode Deposition |
|---|---|---|
| SS3 | 1.62 µg/mm² CMC<br>1.11 µg/mm² Buffer<br>0.58 µg/mm² PQQ/GDH Enzyme System<br>1.39 µg/mm² Structure I Mediator<br>pH 7.2 ± 0.1 | 1.62 µg/mm² CMC<br>1.11 µg/mm² Buffer<br>1.39 µg/mm² Structure I Mediator<br>pH 7.2 ± 0.1 |
| SS4 | 1.14 µg/mm² CMC<br>0.78 µg/mm² Buffer<br>0.41 µg/mm² PQQ/GDH Enzyme System<br>1.95 µg/mm² Structure I Mediator<br>pH 7.2 ± 0.1 | Same as Working Electrode |

The samples were analyzed with a pulse sequence having an initial excitation including two short excitations separated by about 0.25 second followed by a 1 second relaxation. After the initial excitation and relaxation, a sequence of three about 0.375 second excitations separated by two about 1 second relaxations was applied. An output current recorded after about 5 seconds from the application of the initial input signal was used to determine the glucose concentration of the sample.

Tables IV and V, below, provide the statistical hematocrit bias results for SS1 through SS4, where two analyses were performed with each type of sensor strip for each of the 21 blood samples to provide 42 readings. Table IV shows the slope, intercept and I/S ratio for each sensor strip lot, while Table V shows the percentage of readings having biases within ±15/±15%, ±10/±10%, or ±5/±5% of the YSI reference value. For glucose concentrations less than 75 mg/dL bias is expressed as mg/dL (absolute) and for glucose concentrations of 75 mg/dL and greater bias is expressed in percent (relative).

| Sensor | Slope | Intercept | I/S Ratio mg/dL |
|---|---|---|---|
| SS1 | 34.61 | 91.73 | 2.65 |
| SS2 | 32.65 | −115.8 | −3.55 |
| SS3 | 30.76 | −28.00 | −0.91 |
| SS4 | 33.91 | 106.87 | 3.15 |

Table IV

TABLE V

| Sensor | Bias % within ±15% | Bias % within ±10% | Bias % within ±5% |
|---|---|---|---|
| SS1 | 100 | 100 | 93 |
| SS2 | 100 | 97.6 | 64 |
| SS3 | 100 | 97.6 | 93 |
| SS4 | 100 | 97.6 | 67 |

Table IV establishes that each of the sensor strip lots had an I/S ratio of less than 5 mg/dL, thus establishing the superior background signal performance of the strips. The performance of a sensor system may be characterized by the spread of the biases against the reference values. This spread may be measured by the percentage of bias values falling within certain limits, such as ±15 mg/dL/±15% or ±10 mg/dL/±10%. The smaller the limit, the better the performance. Multiple factors, including measurement imprecision and the hematocrit effect, will contribute to the bias values. Normally, the performance is judged by having at least 95% of the data population being within a certain performance limit. Thus, Table V establishes that 100% of the data population from SS1 through SS4 was within the limit of ±15 mg/dL/±15%. Furthermore, more than 95% of the data population from SS1 through SS4 was within the limit of ±10 mg/dL/±10%.

Figure 7A:
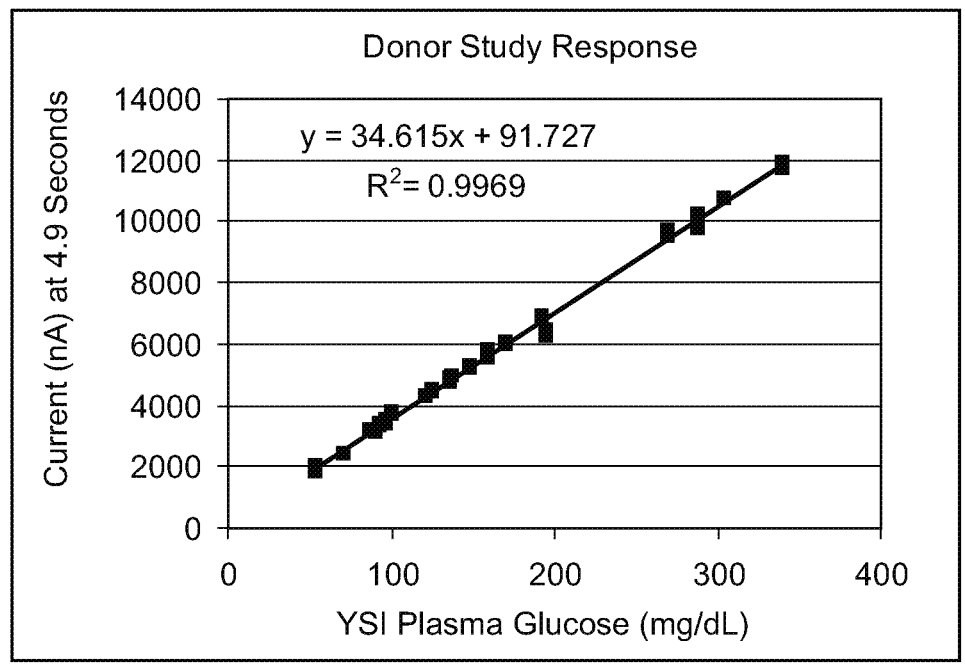
FIG. 7A depicts the dose response curve from a sensor strip for multiple whole blood samples.
Figure 7B:
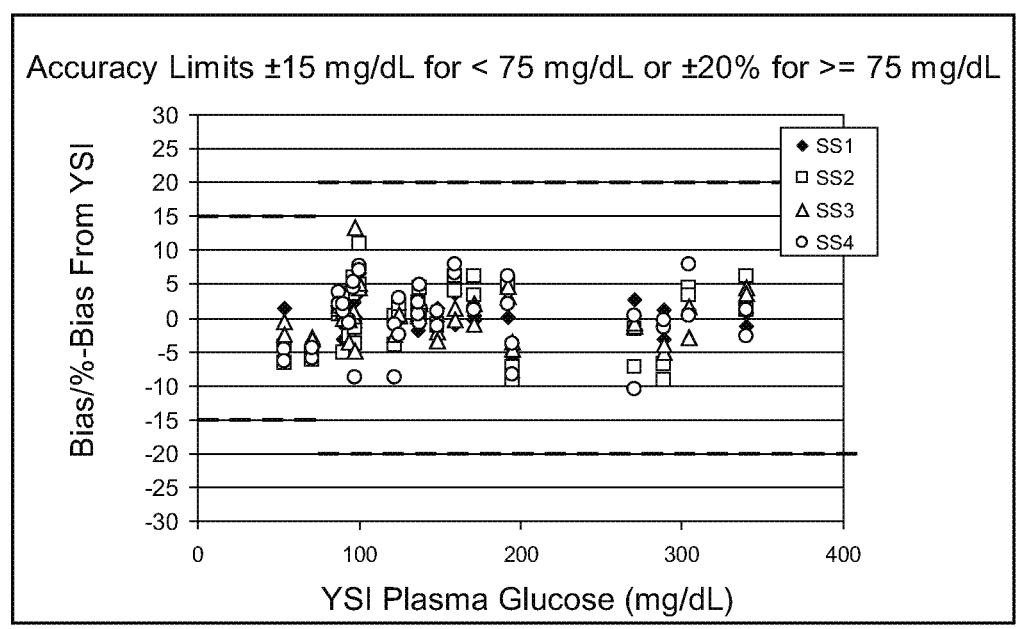
FIG. 7B depicts the absolute hematocrit bias spreads for four manufacturing lots of sensor strips obtained with multiple whole blood samples.

FIG. 7A depicts the dose response curve from the SS1 lot for the 21 whole blood samples. The $R^2$ value of 0.997 established the ability of the strip to provide current values accurately reflecting the actual glucose concentration of the samples. FIG. 7B depicts the bias spreads for lots SS1 through SS4 with the 42 readings from 21 samples across the glucose concentration range in the donor study. The figure establishes that 100% of the bias values for all of the sensor strips fell within ±15%, and that the performance of the SS1 and SS3 manufacturing lots was superior under the conditions of the study with 93% of the data population being within the ±5% limit. The narrow bias spread for the sensor strips may be attributed to the enhanced sensitivity and precision, reflected in the small I/S ratios, and to the small hematocrit effect provided by the strips.

Figure 7C:
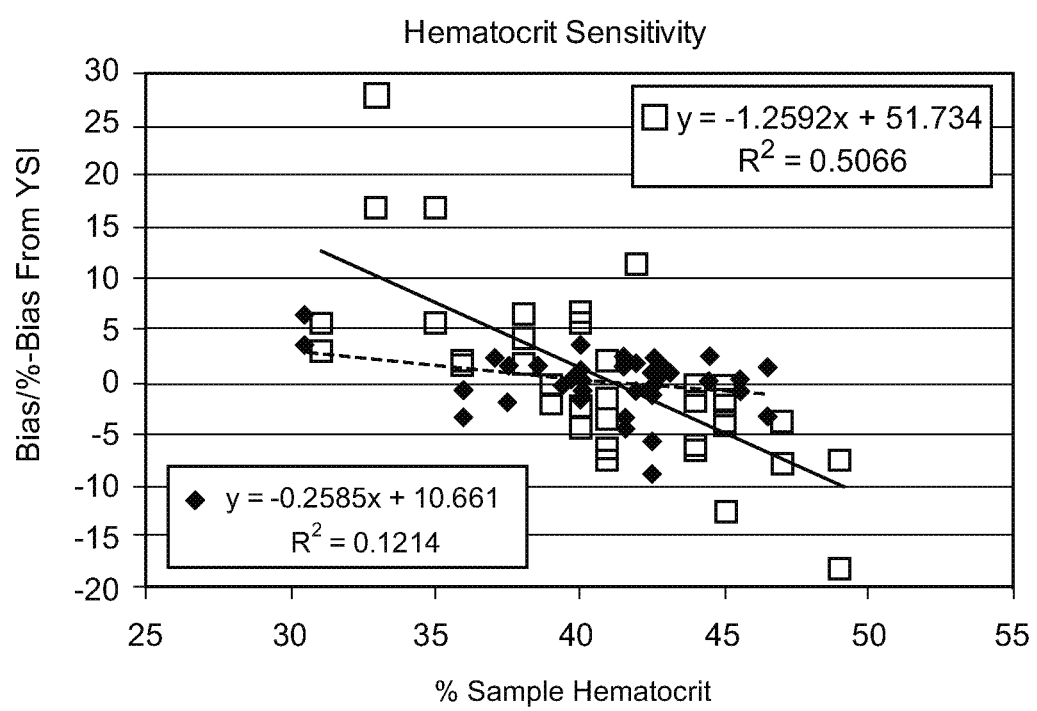
FIG. 7C compares the hematocrit sensitivity between present and conventional sensor strips.

FIG. 7C depicts the hematocrit sensitivity, hematocrit bias in relation to hematocrit content of the sample, obtained from lot SS1 in comparison to a conventional strip having a deposition density of 2.96 µg/mm² for a HEC polymer, 0.69 µg/mm² for a citric buffer, 2.14 µg/mm² for a glucose oxidase enzyme, and 13 µg/mm² for the ferricyanide mediator. A hematocrit sensitivity of −0.26 was obtained for the SS1 lot, while the conventional sensor strips had a slope of −1.26, with numerically larger slope values indicating greater hematocrit sensitivity. Thus, the hematocrit sensitivity of the SS1 lot was approximately 79% less than that provided by the conventional strips.

To provide a clear and consistent understanding of the specification and claims, the following definitions are provided.

"System" is defined as an electrochemical sensor strip in electrical communication through its conductors with an electronic measurement device, which allows for the quantification of an analyte in a sample.

"Measurement device" is defined as an electronic device that can apply an electrical input signal and measure the resulting output signal. The measurement device also may include the processing capability to determine the presence and/or concentration of one or more analytes in response to the output signal.

"Analyte" is defined as one or more substances present in a sample. An analysis determines the presence and/or concentration of the analyte present in the sample.

"Sample" is defined as a composition that may contain an unknown amount of the analyte. Typically, a sample for electrochemical analysis is in liquid form, and preferably the sample is an aqueous mixture. A sample may be a biological sample, such as blood, urine, or saliva. A sample also may be a derivative of a biological sample, such as an extract, a dilution, a filtrate, or a reconstituted precipitate.

"Conductor" is defined as an electrically conductive substance that remains stationary during an electrochemical analysis. Examples of conductor materials include solid metals, metal pastes, conductive carbon, conductive carbon pastes, and conductive polymers.

"Non-ionizing material" is defined as a material that does not ionize during the electrochemical analysis of an analyte. Examples of non-ionizing materials include carbon, gold, platinum and palladium.

"Measurement performance" is defined in terms of accuracy and/or precision. Thus, an increase in measurement performance may be an increase in accuracy and/or precision of the measurement.

"Precision" is defined as how close multiple analyte measurements are for the same sample. Precision may be expressed in terms of the spread or variance among multiple measurements in relation to a mean.

"Accuracy" is defined as how close the amount of analyte measured by a sensor strip corresponds to the true amount of analyte in the sample. Accuracy may be expressed in terms of bias, with larger bias values reflecting less accuracy.

"Bias" is defined as the difference between a measured value and the accepted reference value. Bias may be expressed in terms of "absolute bias" or "relative bias". Absolute bias may be expressed in the units of the measurement, such as mg/dL, while relative bias may be expressed as a percentage of the absolute bias value over the reference value. Either hematocrit or stability bias may be expressed in terms of an absolute bias value or as a percentage. Hematocrit bias uses an analyte concentration obtained with a reference instrument, such as the YSI 2300 STAT PLUS™ available from YSI Inc., Yellow Springs, Ohio, as the accepted reference value. Stability bias uses an analyte concentration obtained from a sensor strip stored at a temperature of −20° C. to substantially reduce thermal alteration of the reagent composition.

"Hematocrit sensitivity" is defined as the degree to which changes in the hematocrit level of a sample affect the hematocrit bias values for an analysis.

"Long-term stability" is defined in relation to sensor strips packaged, such as with foil and desiccant, and stored at −20° C. for 2 or 4 weeks after manufacture versus sensor strips exposed to 50° C. for 2 or 4 weeks, respectively. Storage at 50° C. for 2 weeks may be considered to approximate 18 months of room temperature storage. The average change or deviation for the 0%, 50%, 100%, and 400% hematocrit levels in measurement performance for the 50° C. versus the −20° C. stored strip indicates the long-term stability drift or "stability bias" for the sensor strip. In this instance, an increase in background signal or bias shows a decrease in measurement performance for the sensor strip. Thus, by storing the packaged sensor strips at 50° C. and observing the bias change in relation to −20° C. stored strips, an indication of how much bias will increase for sensor strips remaining on store shelves for various time periods may be obtained.

"Mediator" is defined as a substance that may be oxidized or reduced and that may transfer one or more electrons. A mediator is a reagent in an electrochemical analysis and is not the analyte of interest, but provides for the indirect measurement of the analyte. In a simple system, the mediator undergoes a redox reaction in response to the oxidation or reduction of the analyte. The oxidized or reduced mediator then undergoes the opposite reaction at the working electrode of the sensor strip and is regenerated to its original oxidation number.

"Measurable species" is defined as any electrochemically active species that may be oxidized or reduced under an appropriate potential at the electrode surface of an electrochemical sensor strip. Examples of measurable species include an analyte, a substrate, or a mediator.

"Oxidoreductase" is defined as any enzyme that facilitates the oxidation or reduction of a measurable species. An oxidoreductase is a reagent. The term oxidoreductase includes "oxidases," which facilitate oxidation reactions where molecular oxygen is the electron acceptor; "reductases," which facilitate reduction reactions where the analyte is reduced and molecular oxygen is not the analyte; and "dehydrogenases," which facilitate oxidation reactions in which molecular oxygen is not the electron acceptor. See, for example, *Oxford Dictionary of Biochemistry and Molecular Biology, Revised Edition*, A. D. Smith, Ed., New York: Oxford University Press (1997) pp. 161, 476, 477, and 560.

"Electro-active organic molecule" is defined as an organic molecule lacking a metal that is capable of undergoing a redox reaction. Electro-active organic molecules can behave as redox species and/or as mediators. Examples of electro-active organic molecules include coenzyme pyrroloquinoline quinone (PQQ), benzoquinones and naphthoquinones, N-oxides, nitroso compounds, hydroxylamines, oxines, flavins, phenazines, phenothiazines, indophenols, and indamines.

"Binder" is defined as a material that provides physical support and containment to the reagents while having chemical compatibility with the reagents.

"Average initial thickness" is defined as the average height of a layer in its dry state prior to introduction of a liquid sample. The term average is used because the top surface of the layer is uneven, having peaks and valleys.

"Deposition density" is defined as the mass of a material deposited on an area. For example, when 0.24 µL of a solution containing 2.57 µg of a solid is deposited on a surface having an area of 1.5 mm$^2$, a deposition density of 1.72 µg/mm$^2$ (2.57 µg/1.5 mm$^2$) results.

"Enzyme unit" (U) is defined as the amount of an enzyme system that will catalyze the transformation (oxidation or reduction) of 1 micromole of substrate (analyte) in 1 minute under standard conditions.

"Enzyme activity" or "activity" with regard to an enzyme system is the number of enzyme units per volume. Thus, activity may be given in terms of U/L or mU/mL where 1 U/L=µmol/minute/Liter, for example.

"Redox reaction" is defined as a chemical reaction between two species involving the transfer of at least one electron from a first species to a second species. Thus, a redox reaction includes an oxidation and a reduction. The oxidation portion of the reaction involves the loss of at least one electron by the first species, and the reduction portion involves the addition of at least one electron to the second species. The ionic charge of a species that is oxidized is made more positive by an amount equal to the number of electrons transferred. Likewise, the ionic charge of a species that is reduced is made less positive by an amount equal to the number of electrons transferred.

"Oxidation number" is defined as the formal ionic charge of a chemical species, such as an atom. A higher oxidation number, such as (III), is more positive, and a lower oxidation number, such as (II), is less positive. A neutral species has an ionic charge of zero (0). The oxidation of a species results in an increase in the oxidation number of that species, and reduction of a species results in a decrease in the oxidation number of that species.

"Redox pair" is defined as two conjugate species of a chemical substance having different oxidation numbers. Reduction of the species having the higher oxidation number produces the species having the lower oxidation number. Alternatively, oxidation of the species having the lower oxidation number produces the species having the higher oxidation number.

"Oxidizable species" is defined as the species of a redox pair having the lower oxidation number, and which is thus capable of being oxidized into the species having the higher oxidation number. Likewise, the term "reducible species" is defined as the species of a redox pair having the higher oxidation number, and which is thus capable of being reduced into the species having the lower oxidation number.

"Soluble redox species" is defined as a substance that is capable of undergoing oxidation or reduction and that is soluble in water (pH 7, 25° C.) at a level of at least 1.0 grams per Liter. Soluble redox species include electro-active organic molecules, organotransition metal complexes, and transition metal coordination complexes. The term "soluble redox species" excludes elemental metals and lone metal ions, especially those that are insoluble or sparingly soluble in water.

"Organotransition metal complex," also referred to as "OTM complex," is defined as a complex where a transition metal is bonded to at least one carbon atom through a sigma bond (formal charge of −1 on the carbon atom sigma bonded to the transition metal) or a pi bond (formal charge of 0 on the carbon atoms pi bonded to the transition metal). For example, ferrocene is an OTM complex with two cyclopentadienyl (Cp) rings, each bonded through its five carbon atoms to an iron center by two pi bonds and one sigma bond. Another example of an OTM complex is ferricyanide (III) and its reduced ferrocyanide (II) counterpart, where six cyano ligands (formal charge of −1 on each of the 6 ligands) are sigma bonded to an iron center through the carbon atoms of the cyano groups.

"Coordination complex" is defined as a complex having well-defined coordination geometry, such as octahedral or square planar geometry. Unlike OTM complexes, which are defined by their bonding, coordination complexes are defined by their geometry. Thus, coordination complexes may be OTM complexes (such as the previously mentioned ferricyanide), or complexes where non-metal atoms other than carbon, such as heteroatoms including nitrogen, sulfur, oxygen, and phosphorous, are datively bonded to the transition metal center. For example, ruthenium hexaamine is a coordination complex having a well-defined octahedral geometry where six $NH_3$ ligands (formal charge of 0 on each of the 6 ligands) are datively bonded to the ruthenium center. A more complete discussion of organotransition metal complexes, coordination complexes, and transition metal bonding may be found in Collman et al., *Principles and Applications of Organotransition Metal Chemistry* (1987) and Miessler & Tarr, *Inorganic Chemistry* (1991).

"Handheld device" is defined as a device that may be held in a human hand and is portable. An example of a handheld device is the measurement device accompanying Ascensia® Elite Blood Glucose Monitoring System, available from Bayer HealthCare, LLC, Elkhart, Ind.

"On" is defined as "above" and is relative to the orientation being described. For example, if a first element is deposited over at least a portion of a second element, the first element is said to be "deposited on" the second. In another example, if a first element is present above at least a portion of a second element, the first element is said to be "on" the second. The use of the term "on" does not exclude the presence of substances between the upper and lower elements being described. For example, a first element may have a coating over its top surface, yet a second element over at least a portion of the first element and its top coating can be described as "on" the first element. Thus, the use of the term "on" may or may not mean that the two elements being related are in physical contact with each other.

While various embodiments of the invention have been described, it will be apparent to those of ordinary skill in the art that other embodiments and implementations are possible within the scope of the invention. Accordingly, the invention is not to be restricted except in light of the attached claims and their equivalents.

The invention claimed is:

1. An electrochemical biosensor for determining an analyte concentration in a fluid sample, the biosensor comprising:
    a base;
    a first electrode on the base including a first conductor and a reagent layer, the reagent layer including a mediator having a deposition density of at most 8 μg/mm$^2$ and an enzyme system having a deposition density of at most 0.8 μg/mm$^2$;
    a second electrode on the base; and
    a lid, the lid and the base assisting in forming an opening to receive the fluid sample,
    wherein the biosensor provides a determined concentration value having a stability bias of less than +/−10% after storage at 50° C. for 2 weeks when compared to a comparison biosensor stored at −20° C. for 2 weeks.

2. The biosensor of claim 1, wherein the second electrode includes a second conductor and a second reagent layer.

3. The biosensor of claim 2, wherein the second reagent layer is different in composition from the reagent layer.

4. The biosensor of claim 2, wherein the second reagent layer is the same as the reagent layer.

5. The biosensor of claim 1, wherein the average initial thickness of the reagent layer is less than 8 μm.

6. The biosensor of claim 5, wherein the average initial thickness of the reagent layer is less than 4 μm.

7. The biosensor of claim 1, wherein the enzyme system has a deposition density of at most 0.5 μg/mm$^2$.

8. The biosensor of claim 1, wherein the reagent layer comprises at most 1.3 Units of the enzyme system.

9. The biosensor of claim 1, wherein the reagent layer including a mediator having a deposition density of at most 2 μg/mm$^2$.

10. The biosensor of claim 1, wherein the stability bias is less than +/−5% after storage at 50° C. for 2 weeks when compared to the comparison biosensor stored at −20° C. for 2 weeks.

11. The biosensor of claim 1, wherein the reagent layer further includes a polymeric binder selected from the group consisting of poly(ethylene oxide), polyvinyl alcohol, hydroxyethylene cellulose, carboxy methyl cellulose, and combinations thereof.

12. The biosensor of claim 1, wherein the mediator is selected from the group consisting of 3 phenylimino-3H-phenothiazines, 3 phenylimino-3H phenoxazines, salts thereof, acids thereof, derivatives thereof, and combinations thereof.

13. An electrochemical biosensor for determining an analyte concentration in a fluid sample, the biosensor comprising:

a base;

a first electrode on the base including a first conductor and a reagent layer, the reagent layer including a mediator having a deposition density of at most 8 µg/mm$^2$ and an enzyme system having a deposition density of at most 0.8 µg/mm$^2$;

a second electrode on the base; and a lid, the lid and the base assisting in forming an opening to receive the fluid sample, wherein the biosensor provides a determined concentration value having a hematocrit bias of less than +/−10% for whole blood samples including from 20 to 60% hematocrit.

14. The biosensor of claim 13, wherein the hematocrit bias is less than +/−5% for the whole blood samples including from 20 to 60% hematocrit.

15. The biosensor of claim 13, wherein the average initial thickness of the reagent layer is less than 8 µm.

16. The biosensor of claim 13, wherein the enzyme system has a deposition density of at most 0.5 µg/mm$^2$.

17. The biosensor of claim 13, wherein the reagent layer including a mediator having a deposition density of at most 2 µg/mm$^2$.

18. An electrochemical biosensor for determining an analyte concentration in a fluid sample, the biosensor comprising:

a base;

a first electrode on the base having at least one first layer on a first conductor, the first layer including a reagent layer comprising at most 8 µg/mm$^2$ of a mediator, and an enzyme system at a deposition density of at most 0.8 µg/mm$^2$;

a second electrode on the base; and a lid, the lid and the base assisting in forming an opening to receive the fluid sample, wherein the biosensor provides a determined concentration value having an intercept to slope ratio of at most 20 mg/dL.

19. The biosensor of claim 18 wherein the intercept to slope ratio is at most 10 mg/dL.

20. The biosensor of claim 19, wherein the intercept to slope ratio is at most 6 mg/dL.

21. The biosensor of claim 20, wherein the intercept to slope ratio is at most 1 mg/dL.

22. The biosensor of claim 18, wherein the average initial thickness of the reagent layer is less than 8 µm.

23. The biosensor of claim 18, wherein the enzyme system has a deposition density of at most 0.5 µg/mm$^2$.

24. The biosensor of claim 18, wherein the reagent layer including a mediator having a deposition density of at most 2 µg/mm$^2$.

* * * * *